(12) United States Patent
Meir

(10) Patent No.: US 10,668,296 B2
(45) Date of Patent: Jun. 2, 2020

(54) DEVICE AND METHOD FOR GENERATING ELECTRICAL STIMULATION

(71) Applicant: Marian Meir, Ein-Hod (IL)

(72) Inventor: Marian Meir, Ein-Hod (IL)

(73) Assignee: CARDIFAB LTD., Tsukey Yam (IL)

( * ) Notice: Subject to any disclaimer, the term of this patent is extended or adjusted under 35 U.S.C. 154(b) by 143 days.

(21) Appl. No.: 15/360,584

(22) Filed: Nov. 23, 2016

(65) Prior Publication Data

US 2018/0140859 A1    May 24, 2018

(51) Int. Cl.
*A61N 1/39* (2006.01)
*A61N 1/04* (2006.01)
*H02J 7/34* (2006.01)

(52) U.S. Cl.
CPC .......... *A61N 1/3981* (2013.01); *A61N 1/046* (2013.01); *A61N 1/0492* (2013.01); *A61N 1/3925* (2013.01); *A61N 1/3968* (2013.01); *A61N 1/3993* (2013.01); *H02J 7/342* (2020.01); *H02J 7/345* (2013.01)

(58) Field of Classification Search
CPC ..... A61N 1/3981; A61N 1/046; A61N 1/3968
See application file for complete search history.

(56) References Cited

U.S. PATENT DOCUMENTS

| 4,375,817 | A | * | 3/1983 | Engle | .................. | A61N 1/3962 |
| | | | | | | 607/4 |
| 4,565,995 | A | * | 1/1986 | Stokes | ................ | G01R 22/066 |
| | | | | | | 340/541 |
| 5,395,395 | A | | 3/1995 | Hedberg | | |
| 5,507,781 | A | | 4/1996 | Kroll et al. | | |
| 5,591,211 | A | | 1/1997 | Meltzer | | |
| 6,241,751 | B1 | | 6/2001 | Morgan et al. | | |
| 6,421,563 | B1 | * | 7/2002 | Sullivan | .................... | A61N 1/39 |
| | | | | | | 428/908 |
| 6,441,582 | B1 | * | 8/2002 | Powers | ................ | A61N 1/3975 |
| | | | | | | 320/112 |
| 9,242,116 | B2 | | 1/2016 | Shaker | | |
| 10,004,912 | B1 | * | 6/2018 | Soloway | ............... | A61N 1/3987 |
| 2001/0031992 | A1 | | 10/2001 | Fishler et al. | | |
| 2003/0018361 | A1 | | 1/2003 | Herleikson | | |
| 2003/0080712 | A1 | * | 5/2003 | Tamura | .................... | A61N 1/39 |
| | | | | | | 320/103 |
| 2003/0216785 | A1 | | 11/2003 | Edwards et al. | | |
| 2004/0122476 | A1 | * | 6/2004 | Wung | ...................... | A61N 1/39 |
| | | | | | | 607/5 |

(Continued)

*Primary Examiner* — William J Levicky
(74) *Attorney, Agent, or Firm* — Browdy and Neimark, P.L.L.C.

(57) ABSTRACT

A handheld defibrillation device is disclosed, operated by a single battery cell, and configured to deliver a defibrillation pulse to a subject via defibrillation pads. The defibrillator comprises an energy storage unit comprising a plurality of capacitive elements, a plurality of charger units, each charger unit being electrically connected to the battery cell for electrically charging a respective one of the capacitive elements, and a pulse delivery unit configured and arranged to discharge the electrical charges of the capacitive elements through the defibrillation pads. The charging units and the pulse delivery unit, and various other parts of the defibrillator are specially designed to permit compactly packaging the defibrillator inside a handheld pocketsize housing.

31 Claims, 10 Drawing Sheets

(56) References Cited

U.S. PATENT DOCUMENTS

| | | | |
|---|---|---|---|
| 2006/0142808 A1* | 6/2006 | Pearce | A61N 1/39 607/5 |
| 2009/0318988 A1 | 12/2009 | Powers | |
| 2010/0198287 A1* | 8/2010 | Neumiller | A61N 1/3931 607/5 |
| 2012/0191150 A1* | 7/2012 | Kameli | A61N 1/3956 607/4 |
| 2013/0282079 A1 | 10/2013 | Kallmyer | |
| 2014/0004494 A1* | 1/2014 | Griesser | A61N 1/3993 434/267 |
| 2014/0222095 A1* | 8/2014 | Einy | A61N 1/39 607/5 |
| 2014/0317914 A1* | 10/2014 | Shaker | A61N 1/3993 29/825 |
| 2016/0249846 A1* | 9/2016 | Yoo | A61N 1/36025 600/544 |
| 2017/0106183 A1* | 4/2017 | Silver | A61N 1/39 |

* cited by examiner

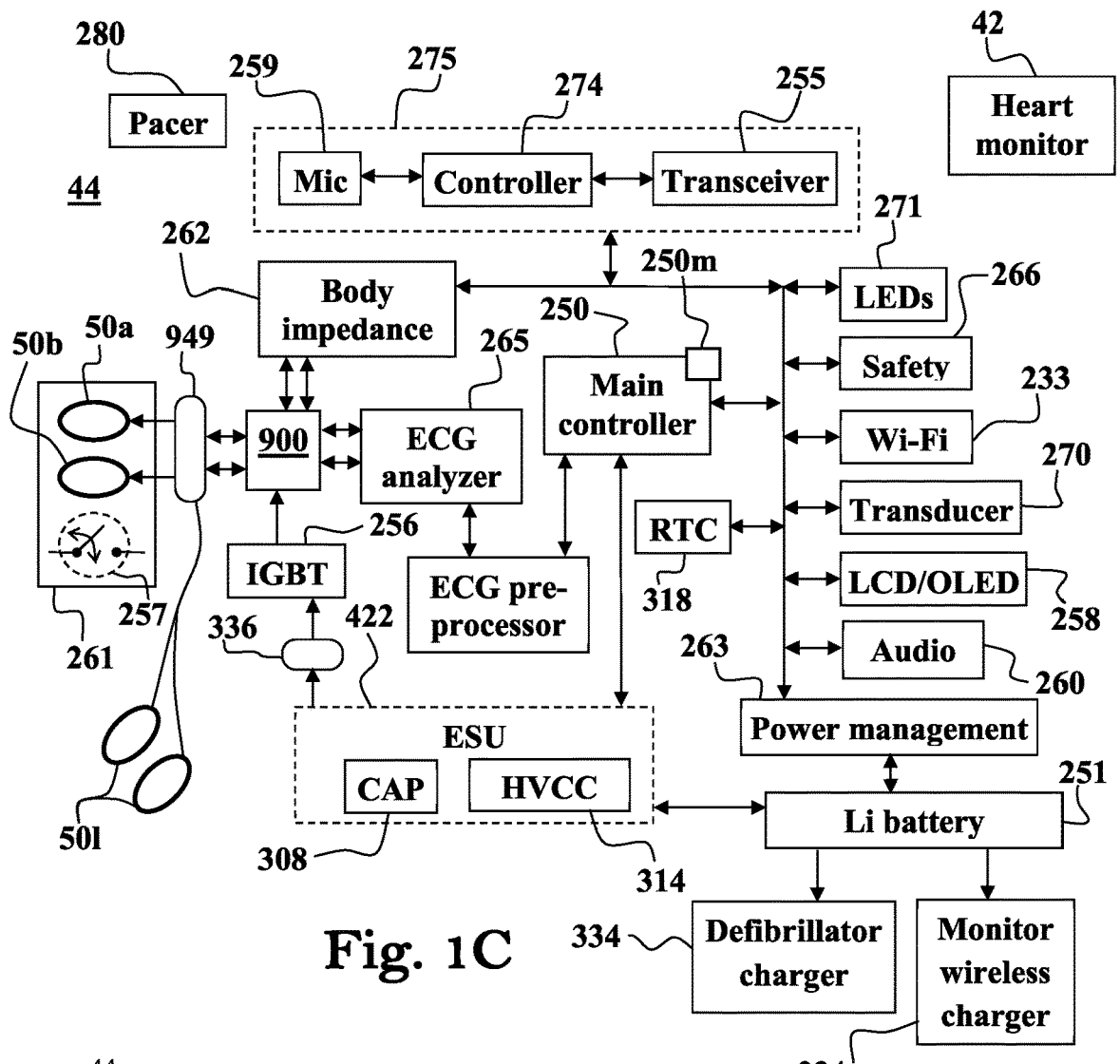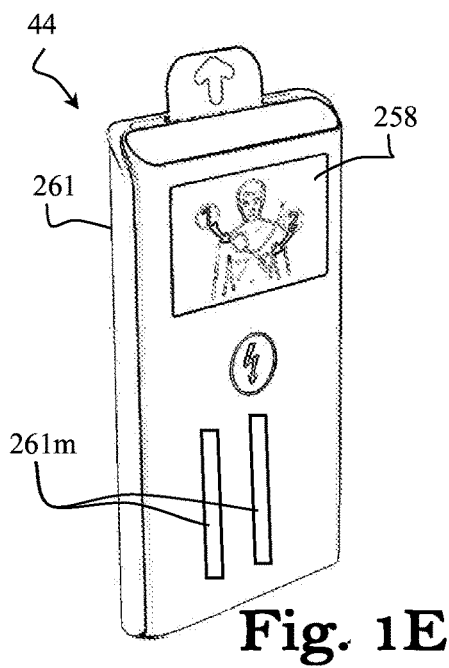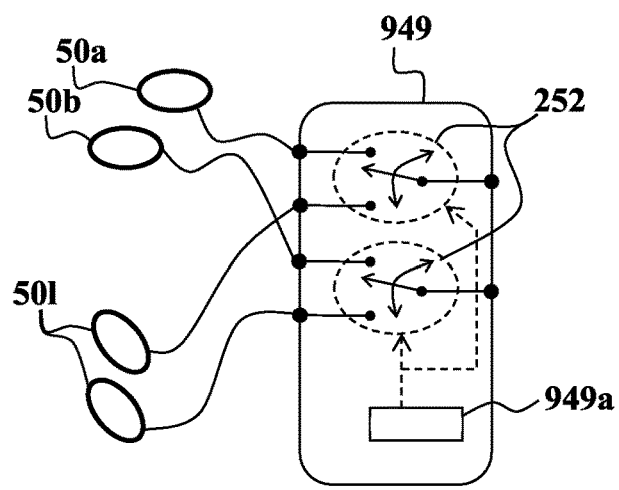
Fig. 1C
Fig. 1E
Fig. 1D

DEVICE AND METHOD FOR GENERATING ELECTRICAL STIMULATION

TECHNOLOGICAL FIELD

The present invention generally relates to devices and methods for external generation and delivery of electrical stimulation to a user, such as a defibrillation pulse.

BACKGROUND

The present disclosure provides techniques for externally generating and delivering electrical stimulation to a user/patient, particularly useful for external defibrillation of cardiac tissue. In external defibrillation applications, high voltage electrical pulses are generated to apply high joule (150 to 360 joules) shocks to the heart of a treated user/patient through electrodes connected to the chest area of the user/patient for treating cardiac dysrhythmias and ventricular fibrillation (e.g., sudden cardiac arrest). The electrical pulse generated by external defibrillators (also referred to herein as defibrillation pulse) is typically a decaying capacitive discharge pulse having a peak voltage between 1000 to 2000 volts, and a time duration of about 10 milliseconds.

The conventional external defibrillators, typically consisted of bulky hospital equipment confined for use in healthcare centers. Technological developments in capacitors and batteries production enabled development of portable defibrillators for use out of healthcare centers (e.g., in ambulances). The introduction of the biphasic defibrillation pulses allowed to significantly decrease defibrillation energy levels, which further led to development of automated external defibrillators that can be used without requiring any clinical skills.

Defibrillation devices and techniques known from the patent literature are briefly described herein below.

U.S. Pat. No. 5,395,395 describes a method for increasing the energy output from a number of charged capacitors each of the capacitors is discharged, one after another, through a load. The capacitors are then coupled in series in successive, different combination, each of which includes a part or all of the capacitors. These combinations are and being discharged, one after another, through the load. Also described an apparatus for increasing the energy output from a number of charged capacitors utilizing a charging circuit, arranged to control the charging of the capacitors, and a controllable switching device, arranged to first connect each of the capacitors to a load for discharge of the capacitors, on after another. The switching device then couples the capacitors in series in successive, different combinations, each of which includes a part or all of the capacitors, and connects the respective combinations to the load for discharge of the series couplings, on after another.

U.S. Pat. No. 5,507,781 suggests to use switches to set the topology and polarity of a circuit that includes capacitors to deliver an electric pulse to a heart during a defibrillation procedure. The waveform of the electric pulse is bi-phasic, in that it is a positive portion of the pulse followed by a negative portion of the pulse. The topology and polarity of the circuit are utilized to produce a waveform that approximates the ideal waveform for the specific situation. The circuit provides for combinations of capacitors variously in series and in parallel and changing the topology and polarity of the circuit during discharge of the capacitors.

U.S. Pat. No. 6,241,751 a defibrillator having an energy storage capacitor network with multiple configurations selected according to patient impedance and desired energy level for delivery of an impedance-compensated defibrillation pulse. The set of configurations may include series, parallel, and series/parallel combinations of energy storage capacitors within the energy storage capacitor network. The impedance-compensated defibrillation pulse may be delivered over an expanded range of energy levels while limiting the peak current to levels that are safe for the patient using configurations tailored for lower impedance patients and limiting the range of defibrillation pulse durations and providing adequate current levels for higher impedance patients. Configurations of the energy storage capacitor network may be readily added to extend the range of energy levels well above 200 joules.

General Description

Automated external defibrillation (AED) devices configured for home use are life saving devices designed to be applied on a chest area of a user by electrode pads, sense heart rhythm of the user, and deliver electric shocks to the user's body if certain cardiac arrest conditions are identified. These devices are typically arranged in form of a suitcase designed for household storage, but they are not designed to be comfortably carried by a user during outdoor activities.

Embodiments of the present application provide a handheld lightweight (e.g. of about 350 grams) AED device of substantially reduced size/dimension, that can be easily placed in a front pocket of a shirt or a pouch, or attached to the user's body by belt and/or straps i.e., freeing the user's hands. Thus, the AED device disclosed herein can be easily carried on (e.g., in/on a clothing article or on the user's body) during day and night time activities, or sleep, and instantly activated by the user, and/or a helper e.g., family member, work colleague, passer-by, to deliver defibrillation shocks to the heart of the user in cardiac specific arrhythmias events.

The size and weight of the defibrillators disclosed herein are considerably reduced in some embodiments by, at least, special designs and arrangements of an energy storage unit (ESU) of the defibrillator, and/or of a pulse delivery unit thereof. In some embodiments, the defibrillator is configured to enter first into a standby mode upon activation of the device, in which the ESU is partially charged to a predefine percentage of the required defibrillation voltage, and thereafter it is fully charged to the defibrillation voltage whenever it is determined that a defibrillation pulse is to be applied to the user's body.

Optionally, and in some embodiments preferably, in comparison with the previous art using bulky relays physically disconnect the pads from the rest of the defibrillator to prevent an accidental electrocution, this invention discloses a miniature motorized electro-mechanical contactor to physically isolates the defibrillation pads from the electronic circuits of the defibrillator at any time except when needed, to prevent an accidental electrocution.

In the following disclosure, the ESU comprises a plurality of serially connected small sized capacitive elements (also referred to herein as a capacitor bank), each having a relatively large capacitance value (e.g., about few hundreds of µF) and its own respective charging unit configured to controllably charge each capacitive element of the capacitor bank to a predefined portion of the total voltage needed for defibrillation. In this way, the serially connected capacitive elements can be safely charged to their maximal required voltage levels (e.g., about 2,000 Volts) without using the voltage equalizing resistors ladder, typically required in such serial connection of capacitive cells, thereby compacting the geometrical dimensions and minimizing power loses of the capacitor bank that, typically, occur in conventional designs due to the discharge currents through the voltage equalizing resistors ladder.

Optionally, and in some embodiments, preferably, the capacitive elements used in the ESU (also referred to herein as "storage capacitors") are meticulously examined for selecting capacitive elements having a leakage current within a 5% limit, which, thus, allow constructing the capacitors bank without the conventional equalizing resistors ladder typically required in such implementations. Thus, in some embodiments, when repairing is needed due to a defective capacitive element of the ESU, the entire capacitors bank is replaced to assure that all capacitive elements of the capacitors bank have the same leakage current characteristics. Thus, in some embodiments, the capacitors bank is a removable unit. Optionally, and in some embodiments, preferably, the capacitive elements in the capacitors bank are inseparably attached to each other (e.g., glued together) to prevent separately replacing a defective capacitive element thereof, and assure that the entire capacitors bank is replaced.

In the ESU, the use of a plurality of capacitive elements having, each, a relatively large capacitance value and small geometrical dimensions (relative to capacitive elements used in the previous art), permits substantial compact designs of the charging units of the defibrillators disclosed herein. Further compactness is achieved by utilizing significantly small sized voltage converters (DC/DC converters) to charge each of the storage capacitors.

As described herein below in details, and illustrated in the drawings, this ESU configuration enables substantially compact arrangements of the plurality of relatively small sized storage capacitors and their respective compact charging units into a compact unit. The pulse delivery unit (also referred to herein as an insulated gate IGBT transistor unit) comprises, in some embodiments, a specially designed low power H-bridge circuit configured to convey the electric charges stored in the storage capacitors bank to the electrode pads of the device as a bi-polar defibrillation pulse. Switching circuitries of the H-bridge are activated in some embodiments, by respective isolated drivers powered by respective driver capacitors. In this way, a single and small voltage converter (DC/DC converter) device is used in the pulse delivery unit to electrically charge the driver capacitors to a level sufficient to drive the IGBT transistors of the H-bridge circuit. With this design, the pulse delivery unit can be also arranged to provide small-sized compact structures.

The small-sized compact arrangements of the ESU, of the pulse delivery unit, and of other components of the defibrillator, as described herein below in details, permits small-sized compact arrangements enabling minimizing the geometrical dimensions of the defibrillator into a handheld device e.g., like a thicker smartphone in shape and size.

In a broad aspect, there is provided a handheld defibrillation device connectable to defibrillation pads and comprising a single low voltage and small size battery cell for supplying electrical power the entire defibrillator device, an energy storage unit comprising a plurality of capacitive elements, and a charger setup configured to independently and separately charge each of the plurality of the capacitive elements for outputting by the energy storage unit a determined high voltage level. Optionally, and in some embodiment preferably, the voltage of the single battery cell is smaller than 5 volts. In some embodiments, the determined high voltage level outputted by the energy storage unit is greater than 1,000 volts.

The charger setup can comprise a plurality of charging circuitries, each of the charger circuitries being electrically connected to the single battery cell and configured to charge a respective one of the plurality of capacitive elements of the energy storage unit. A pulse delivery unit is used, in some embodiments, to discharge the capacitive elements through the defibrillation pads in a desired pulse form into a body of a subject.

Optionally, and in some embodiments preferably, each capacitive element of the energy storage unit is serially electrically connected to at least one other capacitive element of the energy storage unit, and wherein, each charging circuitry of the charger setup is being configured to independently and separately deliver electrical charges from the single battery cell to its respective capacitive element in the energy storage unit, to thereby, build the determined high voltage level over the plurality of serially connected capacitive elements.

One inventive aspect of the subject matter disclosed herein relates to a handheld defibrillation device connectable to defibrillation pads for the application of one or more defibrillation pulses. The defibrillation device comprises in some embodiments a single low voltage small size battery cell, an energy storage unit comprising a plurality of capacitive elements, a charger setup comprising a plurality of electric charger circuitries/charging cells, each of said charger circuitries being electrically connected to the battery cell and configured to charge a respective one of the plurality of capacitive elements, and a pulse delivery unit configured to discharge the capacitive elements through the defibrillation pads in a desired pulse form into a body of a subject.

The capacitive elements can be arranged to implement a capacitors bank using a respective plurality of serially connected storage capacitors as its capacitive elements. The pulse delivery unit can be configured and arranged to discharge electrical charges of the serially connected storage capacitors through the defibrillation pads to a body of a subject.

In some embodiments, the defibrillation device is a handheld flat device having a smartphone-like shape and a thickness smaller than 25 mm.

In some embodiments, each electric charging cell comprises a respective one of the storage capacitors serially connected to at least one other storage capacitor of another cell. Each charging circuitry can be configured to, independently and separately, deliver electrical charges from the battery cell to its respective storage capacitor for obtaining a determined voltage level over the capacitors bank. The charging circuitry of each charging cell is configured, in some embodiments, to independently prevent the voltage level over its respective storage capacitor from exceeding a maximal allowable voltage level on the storage capacitor. Optionally and in some embodiments, preferably, operational features of the storage capacitors are selected to permit the energy storage unit to charge the storage capacitors without a voltage equalizing resistors ladder.

Optionally, and in some embodiments, preferably, the number of serially connected storage capacitors in the energy storage unit varies according to properties of the subject, such as, but not limited to, age and/or weight. Thus, the defibrillation device can be a modular device, which may be manufactured in various, different dimensions and energy storage capacitors.

In some possible embodiments, the pulse delivery unit comprises two upper and two lower IGBT blocks (also referred to herein as switching blocks) arranged in a H-bridge structure configured to discharge the charge stored in the plurality of serially connected storage capacitors through the defibrillation pads in a form of a bi-polar defibrillation pulse. Each IGBT block of the pulse delivery unit can comprise a switching circuitry and a respective capacitive element (also referred to herein as a "driver capacitor") configured to store electrical charge for generating a driving current sufficient for changing the IGBT block into an electrically conducting state for delivering the defibrillation pulse. In this way, the IGBT blocks can be arranged to form a H-bridge circuit configured to couple the defibrillation pads to the energy storage unit (ESU). Each IGBT block comprises a controllable driver unit for the IGBT transistor and a driver capacitor configured to power the controllable driver unit to controllably generate the driving current for changing the state of the respective IGBT block into the electrically conducting state when needed.

Advantageously, the H-bridge comprises a single and small power regulator using a voltage converter to supply electric power from the battery cell to the IGBT blocks of the H-Bridge for charging their driver capacitors. Optionally, and in some, embodiments preferably, the voltage converter comprises a small sized flyback converter (403 in FIG. 4A). In some possible embodiments, the ground terminal of the driver capacitor of each IGBT block is electrically connected to a respective rail of said IGBT block, the high voltage terminals of the switching circuitries of the upper IGBT blocks are electrically connected to the energy storage unit for discharging its capacitive elements, a rail of each one of the upper IGBT blocks is electrically connectable to a respective one of the defibrillation pads, a high voltage terminal of the switching circuitry of each one of the lower IGBT blocks is electrically connected to the rail of a respective upper IGBT block, and the lower rails of the lower IGBT block are electrically connected to an electrical ground of the device The pulse delivery unit is configured in some embodiments, to charge the driver capacitors of the lower IGBT blocks of the H-bridge structure upon activation of the single power regulator/voltage converter. The pulse delivery unit can be configured to charge the driver capacitors of the upper IGBT blocks of the H-bridge structure only after charging the driver capacitors of the lower IGBT blocks, by changing the switching circuitries of the lower IGBT blocks into an electrically conducting state.

In some embodiments, the defibrillation device comprises a control unit configured and operable to activate the charging circuitries of the charger setup of the energy storage unit, activate the power regulator/voltage converter for powering the pulse delivery unit, and to generate control signals for the controllable driver units of the lower switching blocks to charge the driver capacitors of the upper switching blocks after the charging of the driver capacitors of the lower switching blocks. Optionally, and in some embodiments, preferably, the control unit is configured and operable to generate control signals for the controllable drivers to activate a predetermined switching sequence of the switching circuitries of the IGBT blocks and thereby, to discharge the storage capacitors of the energy storage unit in a form of a bi-polar defibrillation pulse. The control unit can be configured to activate the charging circuitries of the charger setup of the energy storage unit and to activate the predetermined switching sequence of the IGBT blocks in response to either a user input or an alarm indication received from an external device.

In a possible embodiment, an impedance measurement unit is used for measuring impedance between the defibrillation pads and for generating measurement data indicative thereof. The control unit is configured and operable to process the measurement data obtained from the impedance measurement unit and to activate the predetermined switching sequence of the IGBT blocks if the measured impedance is within a predetermined range.

The device can also comprise a wireless communication module configured and operable to exchange data with and through a data network. The control unit can be configured and operable to communicate data with a computerized device (e.g., a smart device, such a smartphone of the user) during operation of the defibrillation device.

The device comprises, in some embodiments, a case, a display unit provided in the case, and a movable capsule (also referred to herein as cover) having closed and open states relative to the case. The capsule can be configured and arranged to accommodate the defibrillation pads and their connecting cables and to cover a portion of a display area of the display device in the closed state, to thereby provide at least part of the display visible for displaying information in the closed state. Optionally, and in some embodiments, preferably, the capsule is configured and arranged to hermetically seal the defibrillation pads and the connecting cables contained therein while in the closed state.

The capsule comprises, in some embodiments, at least one charging induction coil configured and arranged to wirelessly charge an external device (e.g., a heart monitor configured to provide wirelessly the ECG related signals of the subject to the defibrillation device). One or more support elements can be provided on the capsule for positioning the external device in proximity to the charging induction coil to maximize the wireless transfer of charging energy thereto. Optionally, the capsule and/or the case of the defibrillator unit may comprise wireless circuitry for wirelessly charging the defibrillator internal single cell battery. Both the capsule and the case may comprise guiding mechanical elements to precisely position the external wireless charger with the respective charging device to maximize the magnetic flux for charging.

Advantageously, the storage capacitors of the ESU may have a leakage current in the range of tens of microamperes, to thereby provide a relatively sure and short self-discharge time for reducing electrical shock hazards.

Another inventive aspect of the subject matter disclosed herein relates to a method of applying a defibrillation pulse to a subject via electrode pads. The method comprising separately and independently charging a plurality of serially connected storage capacitors by a plurality of respective charging units, measuring the overall voltage over the plurality of serially connected storage capacitors and generating measurement data indicative thereof, and processing the measurement data and discharging electrical charges accumulated in the serially connected storage capacitors via the electrode pads upon determining that the voltage over the serially connected storage capacitors reached a predetermined defibrillation voltage level.

In some possible embodiments, the method comprises charging the plurality of serially connected storage capacitors until a predefined standby voltage level is obtained over the serially connected storage capacitors, receiving an indication that the defibrillation pulse is to be applied (e.g., a user input and/or an alarm/alert from an external device), charging the plurality of serially connected storage capacitors until the predetermined defibrillation voltage level is obtained over the serially connected storage capacitors, and discharging electrical charges accumulated in the serially connected storage capacitors via the electrode pads.

To permit the charging of the storage capacitors without a voltage equalizing resistors ladder, the charging process comprises, in some embodiments, comparing the voltage over each storage capacitor with an allowable reference voltage, and halting operation of the respective charging unit used for the charging of the storage capacitor whenever the voltage thereover reaches, or exceeds, the allowable reference voltage. The method may further comprise selecting and matching features of the capacitive elements, such as capacity and leakage current, so as to prevent possible damages that may be caused due to overcharging them. Once matching each other, the capacitive elements can be safely charged to voltage levels of about their maximal allowable voltages without a voltage equalizing resistors ladder.

Optionally, and in some embodiments, preferably, the discharging of the electrical charge accumulated in the storage capacitors comprises using a H-bridge structure of two upper and two lower IGBT blocks powered by a single power source/voltage converter to deliver a bi-polar defibrillation pulse. Each of the IGBT blocks comprises an IGBT transistor circuitry and a respective driver capacitor electrically connected to the power source and configured to accumulate electrical charges for changing the state of the respective IGBT transistor to a conductive state. The method can, thus, comprise activating the voltage converter of the single power source for charging the driver capacitors of the lower IGBT blocks and thereafter turning the switching circuitries of the lower IGBT blocks into a conductive state for charging of the driver capacitors of the upper IGBT blocks by providing an indirect path to the ground through the IGBT's transistors of the lower switching blocks.

The method comprises, in some embodiments, measuring the electric impedance between the electrode pads and applying the defibrillation pulse if the measured impedance is within a predefined impedance range. Additionally, or alternatively, the method comprises measuring ECG signals of the subject and applying the defibrillation pulse if the measured ECG signals are indicative of irregular, or specific abnormality of heart activity.

Yet, another inventive aspect of the subject matter disclosed herein relates to a pulse delivery device for discharging the electrical charge from a capacitors bank through two electrodes. The pulse delivery device comprises two upper and two lower IGBT blocks arranged to form a H-bridge structure and a single power source. Each of the IGBT blocks comprises a controllable IGBT based circuitry, a respective driver capacitor configured to store electrical charges from the power source for changing the IGBT based circuitry into an electrically conducting state, a rail for connecting between ground terminals of the controllable switching circuitry and of the respective driver capacitor. The rails of the lower IGBT blocks being connectable to an electrical ground, and the rail of each upper IGBT block being configured to establish electrical connection with said electrical ground via a controllable switching circuitry of respective one of the lower IGBT blocks.

The pulse delivery circuitry is configured, in some embodiments, to charge the driver capacitors of the lower IGBT blocks of the H-bridge structure upon activation of the single voltage converter. The circuit can be configured to charge the driver capacitors of the upper IGBT blocks of the H-bridge structure after charging the driver capacitors of the lower IGBT blocks, by changing the IGBT transistors of the lower IGBT blocks into an electrically conducting state.

Optionally, and in some embodiments, preferably, the device comprises a controllable driver unit in each of the IGBT blocks. The driver capacitor of each one of the IGBT blocks is configured to power its respective controllable driver unit to controllably generate a driving current for changing the state of the respective IGBT transistor of the IGBT block into the electrically conducting state.

In some embodiments, the common ground terminal of both the driver capacitor of the controllable driver and of the IGBT transistor, of each IGBT block, is electrically connected to the respective rail of the IGBT block, high voltage terminals of the switching circuitries of the upper IGBT blocks are electrically connected to the capacitors bank, the rail of each one of the upper IGBT blocks is electrically connectable to a respective one of the electrode pads, a high voltage terminal of the switching circuitry of each one of the lower IGBT blocks is electrically connected to the rail of a respective upper IGBT block, and the rails of the lower IGBT block are electrically connected to the electrical ground of the device.

In some embodiments, each IGBT block comprises a small sized flyback converter configured to use the same single small size and low voltage battery cell of the device for the simultaneous charging of the respective storage capacitors. The term single cell battery as used herein, means a battery whose voltage is dictated by the manufacturing chemistry, and not by interconnecting it serially with other cells to increase the overall voltage of the battery. By example, typically, a single cell battery based on Li chemistry has a voltage of 3.7V.

It is thus appreciated that the defibrillator devices disclosed herein are powered entirely by a single cell battery.

BRIEF DESCRIPTION OF THE DRAWINGS

In order to understand the invention and to see how it may be carried out in practice, embodiments will now be described, by way of non-limiting example only, with reference to the accompanying drawings. Features shown in the drawings are meant to be illustrative of only some embodiments of the invention, unless otherwise implicitly indicated. In the drawings like reference numerals are used to indicate corresponding parts, and in which:

FIGS. 1A to 1E schematically illustrate a defibrillator according to some possible embodiments, wherein FIG. 1A schematically illustrates the defibrillator in use, FIG. 1B schematically illustrates the defibrillator in a closed inoperative state, FIG. 1C is a functional block diagram showing components of the defibrillator, FIG. 1D schematically illustrates a possible pad connectivity scheme, and FIG. 1E schematically illustrates a defibrillator having a rear side cover;

FIGS. 4A and 4B are functional block diagrams of the pulse delivery unit according to some possible embodiments, wherein FIG. 4A shows the pulse delivery unit components and FIG. 4B shows components of a switching unit of the pulse delivery unit;

FIGS. 6A to 6C are flowcharts illustrating defibrillation processes according to possible embodiments, wherein FIG. 6A shows a possible defibrillation process conducted with an helper, FIG. 6B shows a possible defibrillation process conducted by the user without the assistance of a helper, and FIG. 6C shows a possible defibrillation process comprising a partial ESU charge stage and a charging sequence of the pulse delivery unit;

DETAILED DESCRIPTION OF EMBODIMENTS

Figure 1A:
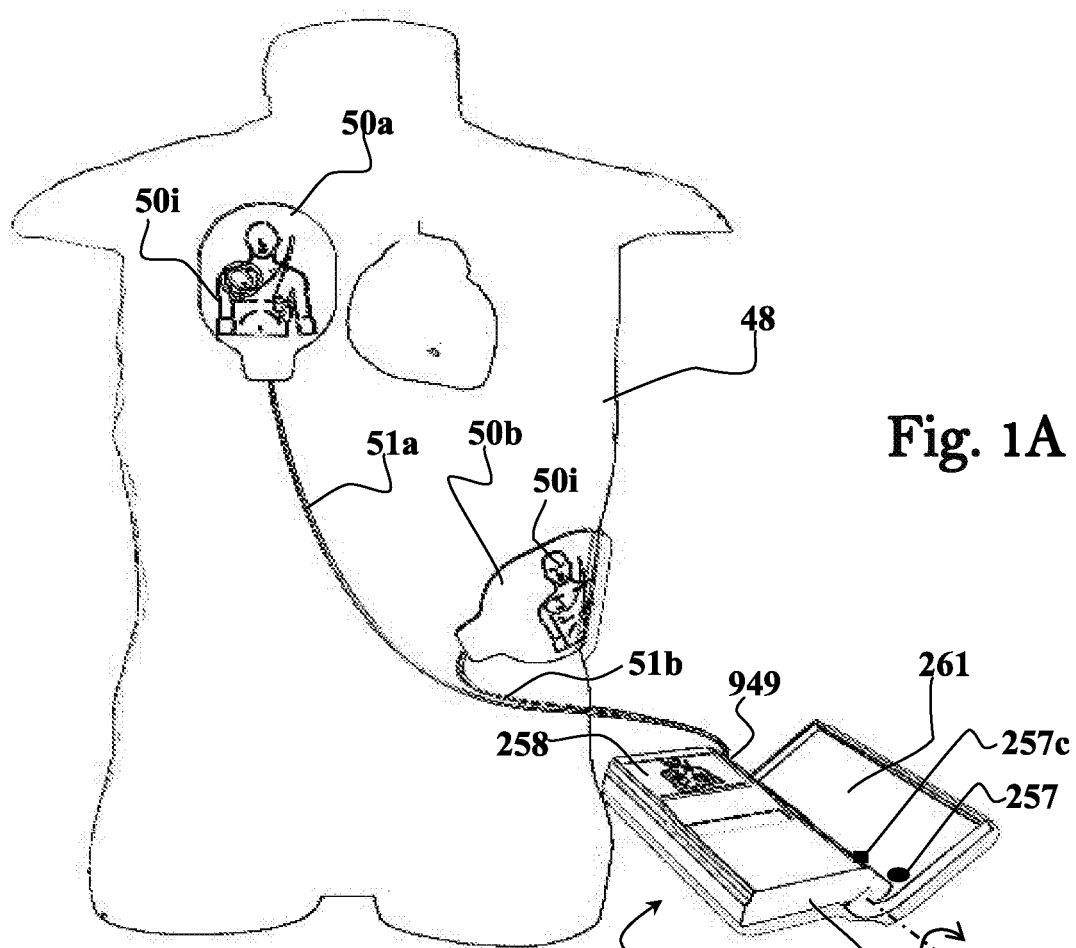

One or more specific embodiments of the present disclosure will be described below with reference to the drawings, which are to be considered in all aspects as illustrative only and not restrictive in any manner. In an effort to provide a concise description of these embodiments, not all features of an actual implementation are described in the specification. Elements illustrated in the drawings are not necessarily to scale, emphasis instead being placed upon clearly illustrating the principles of the invention. This invention may be provided in other specific forms and embodiments without departing from the essential characteristics described herein.

The present disclosure provides defibrillation device configurations and techniques allowing substantial reduction of the geometrical dimensions/size of the device into a small-sized handheld device (e.g., comparable with smartphones such as iPhone 6 of Apple Computers Inc.), which in turn enables implementing a variety of new applications of the defibrillation device. The defibrillation device configurations disclosed herein enable the generation of defibrillation pulses from a small sized rechargeable single cell battery, employing circuitries of substantially reduced sizes.

FIG. 1A schematically illustrates a defibrillator 44, according to some possible embodiments. The defibrillator 44 is shown in an operative state with its case components opened. In this state, the electrode pads 50a and 50b of the defibrillator 44 are attached over anterior area regions of a torso of a user 48. The electrode pads 50a and 50b are electrically connected to the defibrillator 44 by respective electric cables 51a and 51b configured to deliver defibrillating pulses to the body of the user 48 via a high voltage connector 949 of the device. Particularly, the electrode pad 50a is attached over an upper right-side area of the chest of the user 48, and the electrode pad 50b is attached over a lateral area of the left side of the user's abdomen.

It is noted that other configurations/arrangements of the electrode pads on the body of the user 48 may be alternatively used, such as, for example, the trans-thoracic configuration, wherein one electrode pad is applied on an anterior area of the torso and the other electrode pad is applied on a posterior area of the torso.

In some embodiments, the case of the defibrillator 44 is a two-part assembly comprising the housing 45 of the defibrillator and a fitting cover 261 hinged (or not hinged) to the housing 45. Typically, the cover 261 includes a capsule (not shown) structured and arranged for storing the electrode pads 50a and 50b, and the cables 51a and 51b connecting them to the defibrillator 44. As seen, in the open state, the cover 261 is sideway turned to fully expose a display 258 of the defibrillator 44.

The housing of the defibrillator 44 further comprises the electronic circuitries required to operate the defibrillator 44 to produce defibrillation pulses, and the user interface thereof, all of which will be described herein below in details.

Figure 1B:
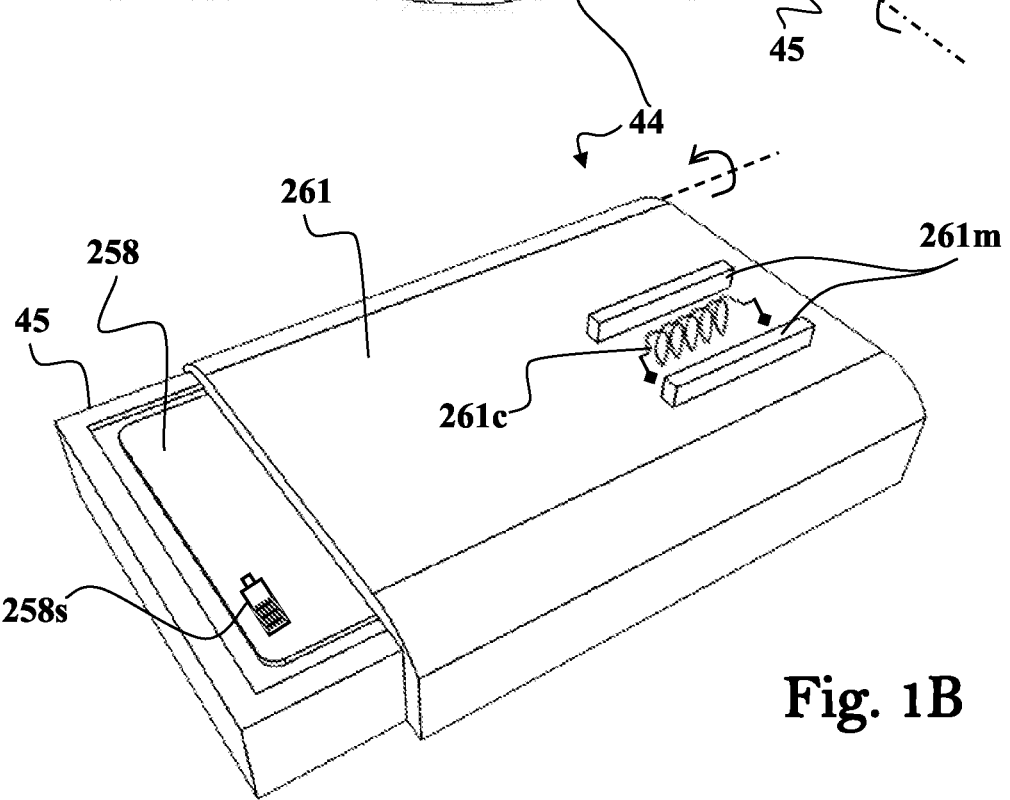

FIG. 1B shows the defibrillator 44 in a closed state wherein the electrode pads and their respective cables are maintained inside the capsule attached to the fitting cover 261. In this state the defibrillation pads and their cables are electrically connected to the defibrillator ready for use. As seen, in the closed state, the cover 261 of the defibrillator partially covers the display 258 e.g., covering, typically, about 75% of the display area, while leaving a portion of the display area visible to show some information, such as but not limited to, the single cell battery charging status 258s, self-test result, emergency messages, and suchlike.

When the cover 261 is opened, an activation switch 257 is changed into a closed/conducting state, which issues an activation signal for commencing a series of operations by the defibrillator 44, such as charging the storage capacitors of the defibrillator 44. Typically, the cover 261 is configured to seal-(waterproof) enclose the electrode pads 50a and 50b and their respective cables, there inside. The high voltage connector 949 (seen in FIG. 1A) is connecting the cables 51a and 51b to the defibrillator 44 which exit cover 261 in a hermetically/waterproof sealed manner in a ready for use state i.e., being in electrical connection via the connector 949. In an emergency event, the cover 261 is turned away from the housing 45 of the defibrillator, such that it becomes unsealed. The defibrillation cables 51a and 51b are then unfolded/deployed, and the electrode pads 50a and 50b are placed on the user's torso 48, as indicated by the graphic illustrations provided on the electrode pads and or indicated by the display 258 and/or indicated by the auditory annunciator of the defibrillator 44. The capsule itself is disposed after the opening of the cover 261, because, once unsealed, the electrode pads and their connecting cables are also disposed.

In some embodiments, the cover 261 of the defibrillator 44 comprises a charging induction coil and relative circuitry 261c configured and arranged to wirelessly charge external accessories, such as, but not limited to, a miniature heart monitor (42 in FIG. 1C). A charging driver (334m in FIG. 1C) of the charging coil 261c can be provided inside the housing 45 of the defibrillator 44. In some embodiments, a flexible cable (not shown) is used to electrically connect e.g., through a miniature connector 257c, between circuitries of the defibrillator 44 and the cover 261 and communicate the signals generated by the activation switch 257, deliver the power from the charging driver to the coil 261c, and connect between any other circuitry provided in the cover 261 and circuitries of the defibrillator.

Optionally, and in some embodiments, preferably, the top side of the cover 261 comprises support elements 261m configured and arranged in such a way as to firmly hold the external accessory being charged by the defibrillator 44 exactly over the charging coil 261c, to thereby optimize the charging.

In another possible embodiment, the cover 261 which contains the capsule with the electrode pads, is assembled over the rear side of the housing of the defibrillator 44 such that it is not obstructing at all the display 258, as illustrated in FIG. 1E. In this specific and non-limiting embodiment, the activation switch (257 in FIG. 1A) is configured and arranged to detect the separation of cover 261 from the housing of the defibrillator 44 when needed. The support elements 261m and the induction coil 261c are placed on the housing of the defibrillator 44 on the same side as the display 258.

FIG. 1C is a functional block diagram of the defibrillator 44, according to some possible embodiments. The defibrillator 44 is operated by a main microcontroller 250 configured and operable to conduct defibrillation pulses generation processes by the device. A real time clock (RTC) 318 is used by the microcontroller 250 in some embodiments, to record a log of events that may occur during the operation of the defibrillator 44, such as the detection of a sudden cardiac arrest or the results of the periodic self-testing of the device. The defibrillator 44 can comprise, in some embodiments, redundant backup circuitries not shown in this example for the sake of simplicity.

During non-operational time periods, various units of the defibrillator 44 can be set into a sleep state, except for the units in the activation block 275, which is configured and operable to awaken the units of the defibrillator 44 into a fully operational state upon receipt of activation signals from an external source. For example, and without being limiting, the external heart monitor 42 is configured in some embodiments to use wireless emergency signal(s) (e.g., activation message(s) coded in sonic/ultrasonic and/or electromagnetic signals), to indicate that activation of the defibrillator 44 is needed.

In some embodiments, the activation block 275 is powered by the rechargeable single cell battery unit 251, optionally comprising a single rechargeable single cell battery, typically, based on Lithium alloys, and its respective power management unit 263, which are configured and operable to drive the very low power microcontroller 274. The microcontroller 274 is configured and operable to operate transceiver 255 and/or the microphone unit 259. The single cell battery 251 is also used to drive all other units/circuitries and devices of the defibrillator 44.

The activation block 275 uses in some embodiments, a low power microcontroller 274, or a suitable circuitry configured as a very low power microcontroller, such as, but not limited to, MPS432 of Texas Instruments. The microcontroller 274 is electrically coupled to a microphone unit 259 configured and operable to receive the external sonic/ultrasonic signals and generate and transfer data and/or signals indicative thereof to the microcontroller 274. The microcontroller 274 is also electrically coupled to a radio frequency (RF) transceiver unit 255 (e.g., Bluetooth), configured and operable to receive the external electromagnetic signals and generate and transfer data and/or signals indicative thereof to the microcontroller 274.

The microcontroller 274 can be implemented as an integral part of the main controller 250, or as a separate part/chip of the device. In some embodiment, only the low power wireless transceiver 255 is active in a reception mode within time windows during the sleep mode, in order to receive any external emergency RF signals e.g., from an external heart monitor. Upon receipt of an emergency signal, the very low power microcontroller 274 of the activation block 275 awakens the remaining units of the defibrillator 44 to change their state into a fully operational mode. Alternatively, or additionally, in some embodiments, the microphone unit 259 is used to capture external sonic/ultrasonic coded emergency signals e.g., from the heart monitor 42, and generate data and/or signals indicative thereof for awaking the defibrillator 44 units. The piezo transducer 270 can be used to emit sonic/ultrasonic coded signals for closing the sonic/ultrasonic communication loop with the external device i.e., heart monitor 42.

In addition to the external RF, and/or sonic/ultrasonic, emergency signals, in some embodiment, a mechanical or optical micro-switch 257 can be also used to activate the defibrillator 44 in response to opening the cover (261 in FIG. 1A) of the device' case/housing 45, typically by a helper/assistant. In response to activation of micro-switch 257, the defibrillator 44 is changed into its fully operational state, independently of the action of activation block 275. Optionally, and in some embodiments, preferably, the defibrillator 44 is regularly maintained in the sleep mode and changed into its fully operational state in response to external activation/emergency signals and/or activation of the micro-switch 257.

Upon receipt of external emergency signals, the state of the defibrillator 44 is changed into an operational state, as described hereinabove. In the operational state, the microcontroller 250 activates the ESU unit 422, which thereupon commences a charging process for generating a defibrillation pulse by the device. The ESU 422 is configured in some embodiments, as a replaceable unit that may be removed from and inserted into defibrillator 44, by example, for repairing.

Once the ESU 422 has accumulated sufficient electric charge in its capacitive elements (of the capacitors bank 308 shown in FIG. 3), the main controller 250 can generate control signals to instruct the ESU 422 to discharge its capacitive elements through the pulse delivery (also referred to herein as IGBT—insulated gate bipolar transistor) unit 256. As described hereinbelow in detail, the pulse delivery unit 256 is configured to generate from the accumulated electric charge of the ESU 422 a defibrillation pulse of a form and time interval suitable for defibrillation. In order to accommodate the electric shock with specific electric impedance of the patient, in some embodiments, the main controller 250 performs during the charging process of the ESU 422, an impedance test between the pads 50a and 50b, using the body impedance measurement unit 262 i.e., the controller 250 determines the amount of energy to be delivered by the defibrillation pulses based on the impedance test performed by the impedance measurement unit 262. The impedance test is also used, in some embodiments, to ensure that the electrode pads 50a and 50b are correctly positioned on the user's/patient's body, and that they are not in contact with an assistant/practitioner of the user/patient. Optionally, and in some embodiments preferably, the impedance test conducted using the impedance measurement unit 262, is used to verify a measured body impedance between the pads 50a and 50b of about 25Ω to 150Ω.

The defibrillator 44 comprises, in some embodiments, a visual indicator/display unit 258 (e.g., comprising an LCD or OLED display) and/or an audio output unit 260 comprising a voice synthesizer, amplifier and speaker (not shown). The audio output unit 260 is configured and operable to generate human comprehendible audio signals, while the transducer 270 is configured and operable to generate loud sonic/ultrasonic signals that can be modulated to transfer encoded information. The main controller 250 can be accordingly configured and operable to utilize the display unit 258, and/or the LED's 271, and/or the audio output unit 260, to convey information to the user and/or the user's assistant. The defibrillator 44 is configured, in some embodiments, to replay previous actions/events conducted/recorded by the defibrillator 44, such as, but not limited to, LED indications outputted via the LEDs unit 271, vocal messages played by the audio output unit 260, and/or data displayed by the display unit 258. Accordingly, the defibrillator 44 is configured and operable in some embodiments, to perform "rewind" functions e.g., responsive to a press button or a touch of a certain region/area of the LED/OLED screen by the user.

The safety unit 266 used in some possible embodiments, comprises independent circuitries configured and operable to monitor sensitive elements of the defibrillator 44 to ensure the detection of hardware or firmware errors/failures, and to resolve such errors, if occurred. For example, and without being limiting, the safety unit 266 is configured and operable in some embodiments to provide alarms/alerts whenever an error is detected, and generate a corrective reset pulse to break infinite firmware loops that may occur.

In some embodiments, a short range wireless communication module (e.g., Wi-Fi) 233 is used in the defibrillator for exchanging data with and through a data network (e.g., the internet) e.g., for downloading a new version of the firmware of the device.

In some embodiments, the defibrillator 44 comprises a charger 334 configured and operable to recharge, wirelessly or not, the single cell battery 251 of the defibrillator 44. Optionally, and in some embodiments, preferably, the defibrillator 44 further comprises a monitor charger 334*m* configured and operable to use the power of the single cell battery 251 of the defibrillator 44 for recharging another external battery, by example, of the heart monitor 42. In some embodiments, the monitor charger 334*m* is configured to wirelessly recharge the battery of the heart monitor 42 e.g., using inductive charging coil(s) configured to transfer electric power from the single cell battery 251 to the battery of the heart monitor 42.

Figure 7A:
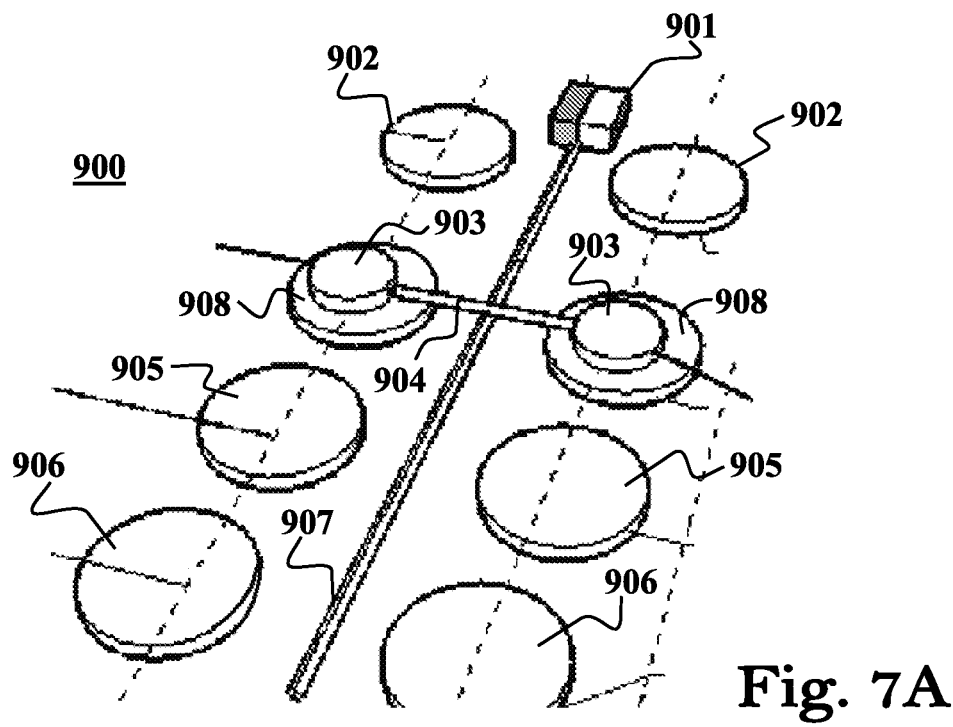
FIGS. 7A and 7B schematically illustrate a miniature motorized electro-mechanical contactor used in some embodiments to physically isolate the defibrillation pads from the electronic circuits of the defibrillator.
Figure 7B:
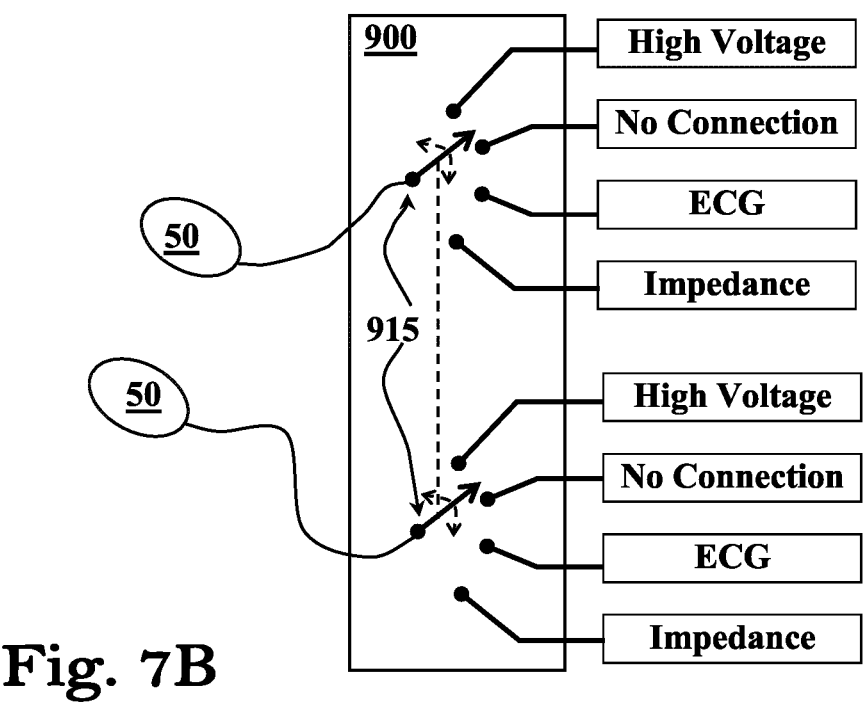

FIGS. 7A and 7B schematically illustrate a miniature motorized electro-mechanical contactor assembly 900 used in some embodiments to physically isolate the defibrillation pads 50 from the electronic circuits of the defibrillator 44. The motorized contactor assembly 900 is configured to establish electrical connection in its respective contact positions between the defibrillation pads 50 and the following circuits: the high voltage circuit (IGBT 256) in position 902; no connection in position 908, the ECG sensor unit (265) in position 905, and the impedance measurement unit (262) in position 906. Additional contact positions may be added for additional functionality such as, for example "pacing", etc.

The motorized mechanical contactor assembly 900 is configured to replace the bulky electro-magnetic relays, and the complicated bulky electronics used therewith, in conventional defibrillators. The motorized contactor assembly 900 utilizes an electro-mechanical mechanism configured to move simultaneously a pair of electrical contacts 903, each of which being electrically connected to a respective one of the defibrillation pads 50, and thereby establish the electrical connection between the pads 50 to the circuitries of the defibrillator in each of the different positions of the contacts 903.

A linear actuator is used, in some embodiments, to move the contacts 903 between the different positions of the motorized contactor assembly 900. The linear actuator comprises a small electric motor 901 (e.g., stepper motor) configured to rotate a threaded rod/screw 907, to thereby slide the horizontal rod 904 therealong by means of a coupling nut (no shown). The sliding horizontal rod 904 can be made of any suitable electrically non-conducting/dielectric material (e.g., plastic), in order for it to bear the high voltage between the contacts 903 when in the high voltage position 902.

The travel time of the contactor 900 from end-to-end of the threaded rod 907 is, typically, less than 2 seconds i.e., from the impedance measurement position 906 to the high voltage position 902, which is insignificant compared to the maximum resuscitation time available to resuscitate a victim of sudden Cardiac arrest of approximately 5 minutes.

Optionally, and in some embodiments preferably, the contacts at positions 902 and 908 are positioned away from each other, to satisfy the appropriate standards concerning high voltages.

A significant advantage of the motorized mechanical contactor assembly 900, is that the contacts 902 and 903 can be manufactured with relatively large contact surfaces in order to reduce their impedance and to support the high defibrillation current of tens of amperes without being damaged by the current, even if the contact material is of lower quality. This permits implementing the electrical contacts of the motorized mechanical contactor assembly 900 by inexpensive electrical contacts (good contacts are expensive), and thereby reduce the associated costs.

Optionally, and in some embodiments preferably, the motorized mechanical contactor assembly 900 comprises sensor elements 915, such as miniature optical sensors, configured to determine exactly the position of moving contacts 903 during their movement along the threaded rod 907.

In some embodiments, an inter-lock connector 949 is used to allow the connection of an external pair of electrode pads 501, while electrically disconnecting the electrode pads 50*a* and 50*b*, without physically detaching them out from connector 949. The connection of the external pair of electrode pads 501 is usable for the self-defibrillating mode described in detail hereinbelow, in which the user can utilize low cost electrode pads 501, instead of the conventional defibrillation pads 50*a* and 50*b*, that are, usually, expensive. The conventional defibrillation pads 50*a* and 50*b* are typically used in emergency situations, and they are expensive as they usually comprise a large scale of illustrations or devices, from simple printed illustrations (50*i* in FIG. 1A) and up to sophisticate electronic circuitries.

The pair of low cost electrode pads 501, typically, does not comprise any additional illustrations, and they are typically used when a user is alone and there is no assistant available for a while during the self-defibrillating mode, as described below. The self-defibrillating mode assumes the user 48 was previously trained and does not need the instructions illustrated of the conventional electrode pads 50*a* and 50*b* about how to use the electrode pads. Typically, a pair of conventional defibrillation pads 50*a* and 50*b* may cost about USD 50, while a pair of regular low cost electrode pads 501 may cost as low as USD 2.

In order to prevent accidental electrocution during the application of a defibrillation pulse, the inter-lock connector 949 is configured in some embodiments, to mechanically and/or electrically, disconnect the conventional defibrillation pads 50*a* and 50*b* upon connection/insertion of the external electrode pads 501. Whenever the external electrode pads 501 are disconnected/taken out from connector 949 (e.g., they are to be disposed), the conventional electrode pads 50*a* and 50*b* are automatically reconnected to the defibrillator 44 at nodes HVA and HVB (Shown in FIG. 4A), respectively.

The inter-lock connector 949 is configured and operable to sustain a high defibrillation voltage of at least 2,500V. With reference to FIG. 1D, in some embodiments, the inter-lock connector 949 comprises a sensor device 949*a* (e.g., optical and/or magnetic) configured and operable to identify the connection/removal of electrode pads 501, and generate data indicative thereof to controller 250. As an alternative to the mechanical automatic switching activated by the connection/removal of the electrode pads 501, the connector 949 further comprises, in some embodiments, controllable electronic switching devices 252, configured and operable to selectively connect the conventional electrode pads, 50a and 50b, or the external electrode pads 501, to the defibrillator 44, according to control/data signals received from the sensor device 949a. In some embodiments, the sensor device 949a is a very low power consumption device, since it needs to remain in an active state at all times, while most of the components of the defibrillator 44 can be changed into a stand-by "sleep" mode when there is no need to generate the defibrillation pulses.

A principal object of some of the embodiments disclosed herein is to provide a defibrillator capable of employing a single battery cell, of substantially low voltage (about or less than 5 Volts), which in some embodiments, is rechargeable, for generating high voltage defibrillation pulses (between 1500 to 2000 Volts). In some embodiments, the defibrillator utilizes a single 3.6 Volts Lithium (Li) battery cell, and configured to generate a defibrillation pulse of approximately 2,000 Volts i.e., greater than the battery cell voltage by a factor (multiplication factor) of about 555.

Figure 2A:
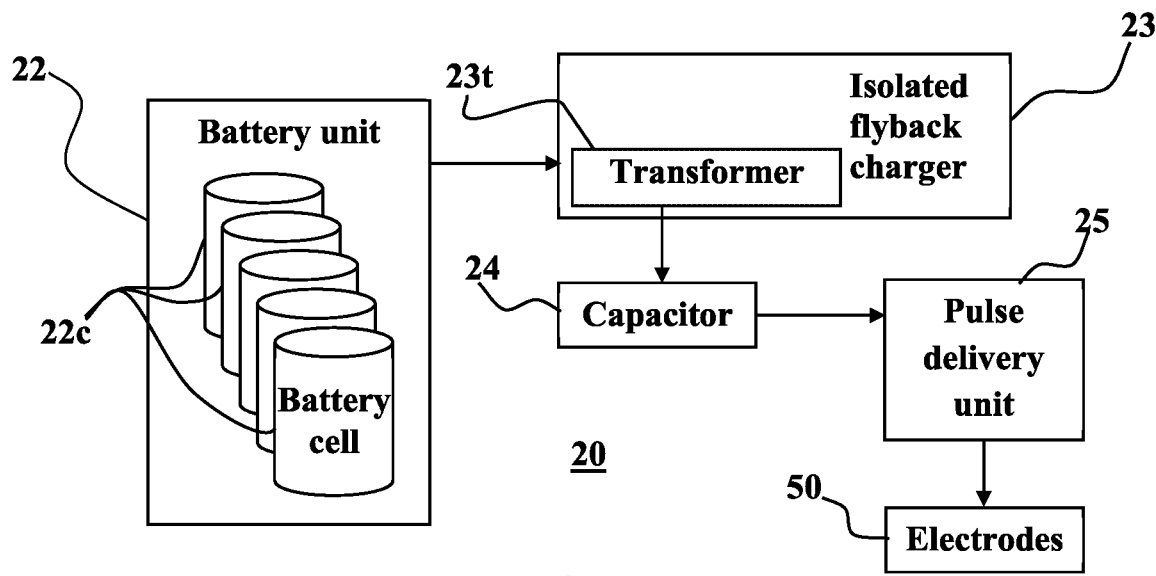
FIGS. 2A and 2B are block diagrams exemplifying improvements and modifications of the defibrillator embodiments disclosed herein, wherein FIG. 2A schematically illustrates a conventional defibrillator and FIG. 2B schematically illustrates a defibrillator according to some possible embodiments.

FIG. 2A exemplifies a conventional defibrillator 20, which typically utilizes a battery unit 22 configured to utilize a plurality of battery cells 22c electrically connected one to the other in series, or in parallel, or in a combined serial and parallel electrical connection, to provide voltage level of about 9 Volts. The voltage of the battery unit 22 is converted by the isolated charger 23 to produce, via the isolating transformer 23t, a voltage of about 1,500 to 2,000 Volts for charging a single storage capacitor, which, thus, typically, has substantially big geometrical dimensions. The electrical voltage charged in the storage capacitors 24 is discharged through the defibrillation electrodes 50 by the pulse delivery unit 25.

For example, the HeartStart defibrillator manufactured by Philips utilizes a non-rechargeable LiMnO2 battery unit of 9 Volts, and its isolated charger is configured to charge a single storage capacitor to a voltage level of about 1,750 Volts, i.e., a multiplication factor of about 194.

Figure 2B:
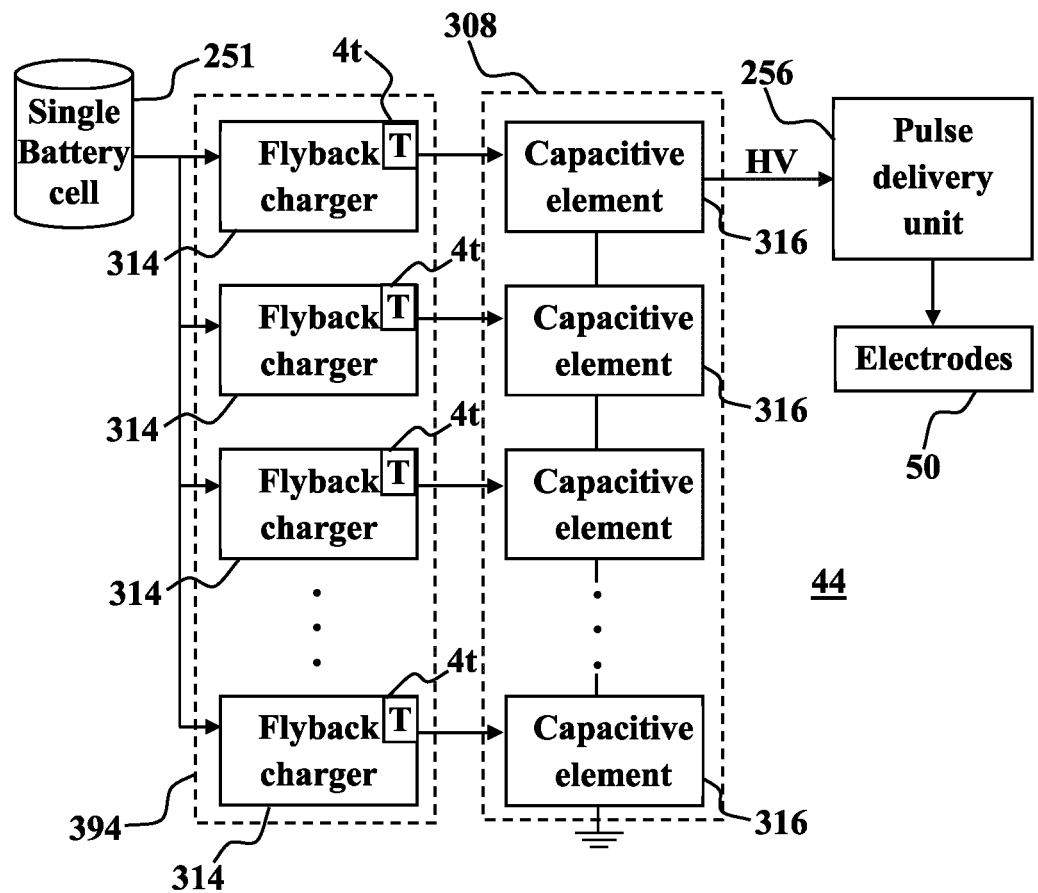

FIG. 2B is a block diagram schematically illustrating a principal structure of a defibrillator 44 according to some possible embodiments of the present disclosure. A single battery cell 251 is used in the defibrillator 44 to charge a set of plurality of serially connected capacitive elements 316 of a capacitor bank 308. Each of the capacitive elements 316 is charged by a respective isolated charger 314, each electrically connected by one terminal thereof to the battery cell 251 and by another terminal thereof to its respective capacitive element 316. The high voltage HV obtained over the serially connected capacitive elements 316 of the capacitor bank 308 is discharged, when needed, through the defibrillation electrodes 50 by a specially designed pulse delivery unit 256.

There are outstanding advantages of using a single battery cell to generate defibrillation pulses by the defibrillator 44. In particular, the geometrical dimensions of single low voltage battery cell 251 are essentially smaller than geometrical dimensions of the multiple cell battery 22 of the conventional defibrillator 20. As shown in FIG. 2B, the exceptionally large multiplication factor of the voltage conversion of the defibrillator 44 (×555), utilizing a single substantially small and low voltage battery cell 251, is achieved by using a setup 394 of multiple DC/DC isolated flyback converters 314. Each of the converters 314 is adapted for charging a respective one of the serially connected capacitive elements 316 of the capacitors bank 308 to a fraction of the total high voltage HV needed for generating a defibrillation pulse, whereas, in the conventional defibrillator 20 of the previous art, a single flyback converter is required to charge the capacitive element 24 to the entire high voltage level required for generating the defibrillation pulse.

The distributed flyback convertors setup 394 yields further reduction of the overall geometrical dimensions of the handheld defibrillator 44. In particular, the single flyback charger 23 of the conventional defibrillator 20 is required to output approximately 2,000 Volts via the isolation transformer 23t, which has to withstand a high voltage of about 2,000 Volts. This means that a substantially great number of wire turns are required in the secondary coil of the transformer 23t to sustain the high voltage multiplication factor, and that relatively thick wires are required to sustain the large charging current thereby supplied e.g., DATATRONICS Inc. 4283 series transformer has a cube shape 2.5×2.5×2.5 cm=15.625 cm$^3$ flyback isolating transformer.

In some embodiments, each charger 314 of the distributed flyback chargers setup 394 utilizes a respective isolation transformer 4t e.g., a 10×10×4 mm BPM15 transformer manufactured by muRata Ps. For example, for a flyback charger setup 394 of five flyback chargers 314, each transformer 4t is required to sustain about 400V, and, with each isolation transformer 4t having a volume of 0.4 cm$^3$, a total volume of 5×0.4=2 cm$^3$ is occupied by the isolation transformers 4t. Obviously, the volume occupied by the isolation transformers 4t of the setup 394 is substantially smaller than the volume occupied by the isolation transformer 23t used by the single isolated flyback charger 23 of the conventional defibrillator 20. In addition, the isolation transformer 23t used in the conventional defibrillator 20 also limits the thickness of the defibrillator 20 to at least than 2.5 cm, while the distributed flyback setup 394 doesn't have not this limitation and advantageously employed in possible embodiments to yield substantially thinner defibrillator designs.

Figure 3:
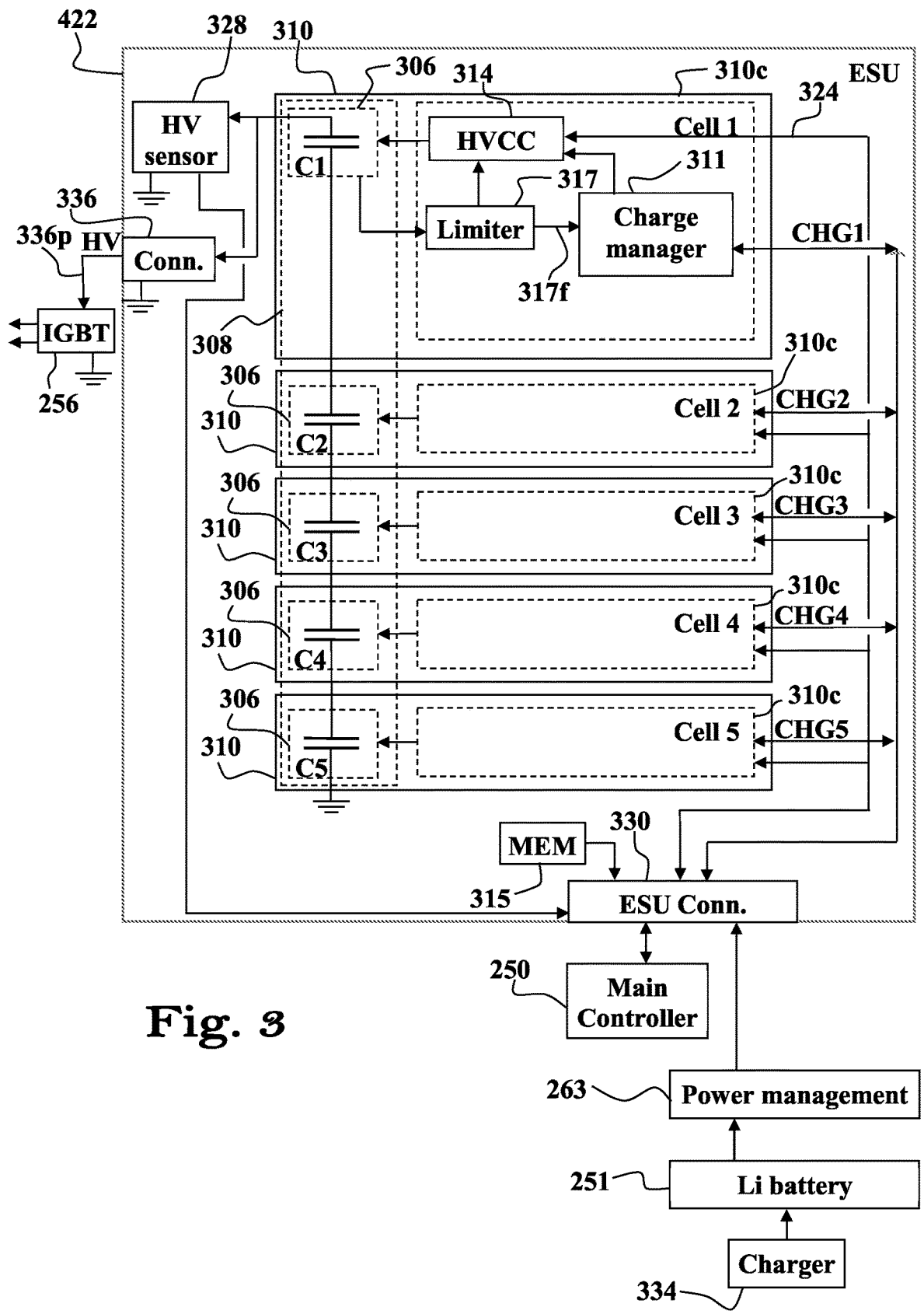
FIG. 3 is a functional block diagram showing the energy storage unit of the defibrillator according to some possible embodiments.

FIG. 3 is a functional block diagram schematically illustrating the ESU 422, according to some possible embodiments. Optionally, and in some embodiments, preferably, the ESU 422 is configured as a replaceable unit of the defibrillator 44. Unlike charge storage units of conventional defibrillator devices, the ESU 422 can be replaced, by example, for repairing or after a predefined time period, and/or after a predefined number of times that the ESU 422 has been activated to generate defibrillation pulses or for self-testing.

The ESU 422 comprises a plurality of serially connected, generally very similar (or identical) capacitive elements 306, C1, C2, . . . , Cn (where n>1 is a positive integer), arranged to assemble a capacitor bank 308. Optionally, and in some embodiments, preferably, the production of the ESU 422, comprises a selection of storage capacitors 306 that have dispersions smaller than approximately 5% in their capacitances, and that their leakage currents are within a defined tolerable range (e.g., of about 5% one relative to other). In some possible embodiments, each storage capacitor 306 is a 500 μF capacitor having a maximum operating voltage of 380V.

Due to the selection of capacitors having matching parameters, and in contrast to typical capacitors banks, embodiments of the capacitors bank 308 do not require the typical resistors ladder/network of voltage equalizing resistors respectively connected in parallel to each capacitor 306 for protecting the capacitive elements from being over charged to voltages exceeding their allowed tolerable maximal voltage. In this way, since the protective ladder/network of resistors is not required in the capacitor bank 308, substantially compact small-sized configurations are achieved for the ESU 422 of the defibrillator 44. In addition, these embodiments of the capacitors bank 308, without the voltage equalizing resistors ladder, further reduce the power consumption and improves the efficiency of the defibrillator 44, by preventing the discharge currents typically passing through the equalizing resistors.

The ESU 422 is modular in the sense that it may be modified according to the defibrillation pulse energy required for the specific user of the device. The number of storage capacitors 306 can be, accordingly, varied, which, in some embodiments, may comprise between 4 to 8 storage capacitors 306. A greater number of storage capacitors 306 enables the defibrillator to generate a stronger electrical pulse having greater energy, to the user. Accordingly, the amount of electrical energy required to defibrillate a small child is storable in some embodiments, in four or less, serially connected capacitive elements 306 of the ESU 422, whereas seven or more storage capacitors 306 may be required to store the electrical energy required to defibrillate an obese adult. The ESU 422 suitable for a child, comprising in some embodiments only three or four storage capacitors 306, and therefor has smaller dimensions, which correspondingly fits the geometrical dimensions required of a defibrillation device designed for the body of a child.

In the specific and non-limiting example shown in FIG. 3, five storage capacitors 306 are used in the ESU 422, but as explained hereinabove, a greater, or smaller, number of storage capacitors 306, can be used in the ESU 422. Furthermore, in veterinary defibrillators intended to defibrillate an animal of greater or smaller body mass, a greater or smaller number of storage capacitors 306 is used in the ESU 422 (greater or smaller than five).

Optionally, and in some embodiments, preferably, each storage capacitor 306 is a cylindrical element having a radius of about 10 mm and a length of about 50 mm i.e., having a volume of about 15.7 cm$^3$. With these geometrical dimensions, the volume of five capacitive elements 306 is approximately 78.5 cm$^3$. In possible embodiments, the five capacitors, C1, C2, . . . , C5, are arranged in close proximity one adjacent the other, with a flat form factor of a rectangular parallelepiped, having height of about 20 mm, and a volume smaller than 100 cm$^3$. It is noted that this volume of the ESU 422 is smaller than ⅓ of the volume of a comparable capacitor used in conventional defibrillators known in the art having the same electrical characteristics, such as the 100 microF, 2,000 VDC capacitor fabricated by ICAR, Italy. In addition, the flat form factor enhances the portability of the ESU 422, and also of the defibrillator 44.

In alternative embodiments, the capacitive elements, C1, C2, . . . , C5, are arranged in a form factor that is different from a rectangular parallelepiped, in a structure comprising, for example, curved and/or flat sides, and which is still significantly smaller than the volumes of capacitors of defibrillator devices of the prior art. The different form factor may be selected to accommodate differently shaped defibrillators, which in turn may be selected to enhance the user's or assistant's comfort.

The storage capacitors 306 can use custom built capacitors, or off-the-shelf capacitors such as, but not limited to, photoflash capacitors. Photoflash capacitors are specifically engineered for electronic photoflashes and for low impedance rapid discharge applications, which are similar to defibrillation discharges. Thus, photoflash capacitors feature high surge discharge currents, which may be significantly large, typically in the order of up to 40 A, required during defibrillation. Photoflash capacitors also have high reliability and long shelf life. Their operating temperature ratings are typically up to 55° C., which is sufficient for the operational environment of the personal defibrillator device disclosed herein, or of a public indoors defibrillator.

The leakage currents of such photoflash capacitors will self-discharge the capacitors within a relatively short time after being used in the defibrillation process, thus eliminating any potential electric shock hazard to the assistant or the user. On the other hand, since the electrical charge stored in the storage capacitors 306 is used within a short time of the storage (e.g., in the range of 10 to 30 seconds), the leakage currents will not reduce the efficiency of operation of the capacitive elements in the ESU 422. It is noted that the defibrillation standard allows a decrease of the capacitors voltage due to self-discharge of only 10% in a 15 seconds time interval.

In the ESU 422, each storage capacitor 306 is configured as part of a respective, generally similar, ESU cell 310. FIG. 3 exemplifies use of five ESU cells, Cell1, Cell2, . . . , Cell5. Each ESU cell 310 comprises storage capacitor 306a charging unit 310c configured for independently and separately charging its respective storage capacitor 306. The charging unit of each ESU cell 310c comprises a high voltage charging circuit (HVCC) 314 electrically coupled to the single cell battery via the supply line 324, a limiter circuit 317, and a cell charge management unit 311. In some embodiments, the HVCC 314 comprises a flyback converter configured to charge its respective capacitor Ci (where i is a positive integer). With this configuration of the ESU 422, the storage capacitor 306 of each ESU cell 310c is separately charged by its respective HVCC 314, independent of the charging process conducted in the other ESU cells 310c.

Upon receipt of a charge control signal over the respective charge control line CHGi, the charge management unit 311 activates the respective HVCC 314 with the voltage provided from the single cell battery on the supply line 324 for charging the respective storage capacitor 306. The limiter 317 is configured to monitor the voltage over the respective storage capacitor 306, and to stop the power supplied from the single cell battery to the storage capacitor 306 by the HVCC 314 before the voltage over the capacitive element reaches a maximal allowable voltage value, to thereby prevent damage thereto due to overcharging. The limiter 317 is thus, an emergency circuit configured to stop the charging of a respective storage capacitor 306 of the capacitor bank 308 when its voltage dangerously reaches the maximal allowable voltage limit, as indicated by the capacitor's manufacturer.

The high voltage (HV) sensor 328 is used to stop the charging of all the storage capacitors 306 in the capacitor bank 308 when a certain high voltage is reached. The HV sensor 328 is configured to measure the total voltage on the series of capacitors C1 to C5 and generate measurement data indicative thereof, and provide the same to the main controller 250 via the connector 330. The controller 250 is configured to process the measurement data from the HV sensor 328, and remove the charge control signals from the charge lines CHGi whenever it is determined from the measurement data that the total voltage of the series of capacitors C1 to C5 is sufficient for delivering a defibrillation pulse to the user.

In some embodiments, each limiter 317 is implemented to comprise a voltage reference circuit and a comparator circuit, configured to compare the voltage on the respective capacitor Ci with the reference voltage, and to stop the charging of the capacitor Ci whenever the voltage thereover reaches a voltage level higher than the reference voltage. The charge manager 311 comprises a circuitry configured to receive, at one side thereof, the controller's CHGi signal, to electrically charge the capacitor Ci, and at other side thereof, the feedback signal 317f from the limiter 317 used to stop, suspend, the charging of the capacitor Ci.

In some embodiments, single cell Li battery e.g., CGA523436B manufactured by Panasonic Corporation of Secaucus, N.J., is used to provide the battery voltage to all the HV charging circuits 314 in parallel. It is however noted that any other suitable number and type of rechargeable batteries can be used for charging the storage capacitors 306 of the capacitors bank 308.

The HV charging circuit 314 comprises in some embodiments, a flyback converter/charger (buck-boost converter using coils of an isolating transformer as its inductors), utilizing a pulse transformer. Since the HV charging circuit 314 of each ESU cell 310 is required to charge the respective storage capacitor 306 of the cell to a voltage of only about 380V, the dimensions of the flyback pulse transformer (not shown) can be relatively small. In some embodiments, the pulse transformer e.g., the BPM15 transformer, manufactured by muRata Ps, has dimensions of 10×10×4 mm i.e., occupying a volume of about 0.4 cm$^3$ per transformer in each ESU cell e.g., for the ESU unit 422 comprising five ESU cells 310, the total volume of the fly-back transformers is about 2 cm$^3$.

This design of the ESU 422, enabling use of small sized pulse transformers, provides a significant reduction in the dimensions (i.e. volume) of the defibrillator 44 as compared to the conventional defibrillator devices used nowadays, which has to have an isolation of typically 1500V rms and which is a cubically shaped transformer having a side size of about 25 mm (e.g., the 4283-1200 Datatronics Romoland Inc.) device which has a volume of about 15.6 cm$^3$, much larger than the total volume of transformers calculated above.

The small dimensions of the HV charging circuit 314 described above enable substantially compact designs of the ESU 422, by packaging its components to occupy volumes that are significantly smaller than the packaging volumes required in the conventional defibrillators.

The memory unit 315 is optionally a non-volatile memory unit used in the ESU 422 to record the overall time of the of the ESU from its initial production time, regardless of whether the ESU is in operational use, or not being used, to generate defibrillating pulses.

In some embodiments, the time count recorded in memory 315 of the replaceable ESU 422 is read whenever it is installed in a defibrillation device 44. During the manufacturing process, both the number of charge/discharge cycles performed by ESU 422, and the time elapsed from the time of production of the ESU 422, are assigned limiting values to be inspected by the defibrillator 44. The main controller 250 of the defibrillator 44 is accordingly configured and operable to trigger an alarm whenever it is determined that the number of charge/discharge cycles performed by the ESU 422, and/or the time elapsed since fabrication of the ESU 422, reached or exceeded the respective maximal allowable factory setting parameters, typically regardless of whether the ESU 422 was, actually, used (or not used) to apply defibrillation pulses. Whenever one of these factory setting parameters is attained (or exceeded), the storage capacitors 306 may be disposed of, or may be returned to the manufacturer for refurbishing.

As explained hereinabove, the high voltage sensor 328 is configured and arranged to measure the voltage across the serially connected storage capacitors 306, C1, C2, . . . , C5, and generate data indicative thereof. This data is typically needed during self-testing of the ESU 422, or when the ESU 422 is being charged to generate a defibrillation pulse. Accordingly, the main controller 250 of the defibrillation can be configured and operable to use the measurement data from the voltage sensor 328 for monitoring the voltage across the serially connected storage capacitors 306. In addition, the voltage across each storage capacitor 306 is also monitored by the respective limiter 317 of each ESU cell 310 and/or by its respective HVCC 314.

The disposable ESU 422 comprises in some embodiments, at least one low voltage and at least one high voltage connectors, as follows:

1. The high voltage connector 336 is configured and operable to electrically couple the serially connected storage capacitors 306 of the capacitors bank 308 of the ESU 442 to the pulse delivery (IGBT) unit 256, and transfer to it the high voltage electrical charges generated by the ESU 442. Optionally, and in some embodiments preferably, the high voltage connector 336 comprises an automated circuit breaker configured and operable to protect users/technicians handling the ESU 442, by automatically disconnecting the ESU 442 from the IGBT pulse delivery unit 256 whenever the ESU 442 is removed from defibrillator 44. For further protection, the high voltage connector 336 can be configured as a female connector on the ESU side, in order to prevent unintended human contact with its pins. Typically, connector 336 is configured and arranged to sustain an operating voltage of at least 1500 Vrms, and to transfer electrical currents of about 40 Ampere, albeit for a relatively short time of the order of a few milliseconds; and 2. The low voltage connector 330 configured and arranged to enable exchange of low voltage control signals and data between the ESU 442 and the circuitries of the defibrillator 44. For example, and without being limiting, the communicated signals can comprise control and data from/to the RTC 315 of the ESU 442, signals/data from/to the HV sensor 328, and control and data from/to the controller 250, and power supply from the single cell battery 251.

As described hereinabove, the ESU 422 comprises a set of serially connected storage capacitors 306. While this arrangement reduces the capacitance of the capacitor bank 308 relative to the capacitance of each storage capacitor 306, this arrangement leads to distinct advantages, such as, inter alia, lower overall voltage requirements, smaller sized electric components, and an adjustable form factor. Furthermore, even in the event of failure of one of the storage capacitors 306 (e.g., if short circuited), or of its charging circuities, this serial arrangement of the capacitor bank 308 can still provide a high fraction of the required electrical defibrillation charge e.g., 80% of the defibrillation charge in embodiments employing five capacitive elements 306.

Optionally, and in some embodiments, preferably, the ESU cells 310 are configured and operable to permit the charging of the storage capacitors 306 to their maximum operating voltages only for predetermined short time periods (e.g., up to 5 minutes, according to the capacitors manufacturer's specifications). In this charging scheme, each storage capacitor 306 is charged to a somewhat lower partial-charge voltage (e.g., 60% to 75% of the maximal voltage) for an unlimited time, and whenever conditions for applying a defibrillation pulse are fulfilled, the storage capacitors 306 are charged to their maximal operating voltages, or to another lower voltage level defined based on the impedance measurement received from the impedance measurement unit 262.

For example, in some embodiments, the storage capacitors 306 are rated to operate at a maximum voltage of about 380 Volts for 5 minutes, and at a lower voltage of about 350 Volts indefinitely. This property is used, in some embodiments, to extend the functional life of the capacitive elements 306, by initially charging the storage capacitors 306 only up to their defined lower voltage range (e.g., 350 Volts), and then, whenever receiving control signals indicating that defibrillation is to be applied to the user, charging the storage capacitors 306 to their defined maximum voltage. An example of such a two-stage charging scheme is also described hereinbelow with reference to flowchart 460 shown in FIG. 6A.

In some embodiments, the ESU 422 comprises six capacitive elements, each configured to be charged to about 330 Volts, and the limiters of the charging cell unit 310c are configured to permit a maximal voltage of up to 350 Volts to evolve over each the capacitive elements.

Figure 4A:
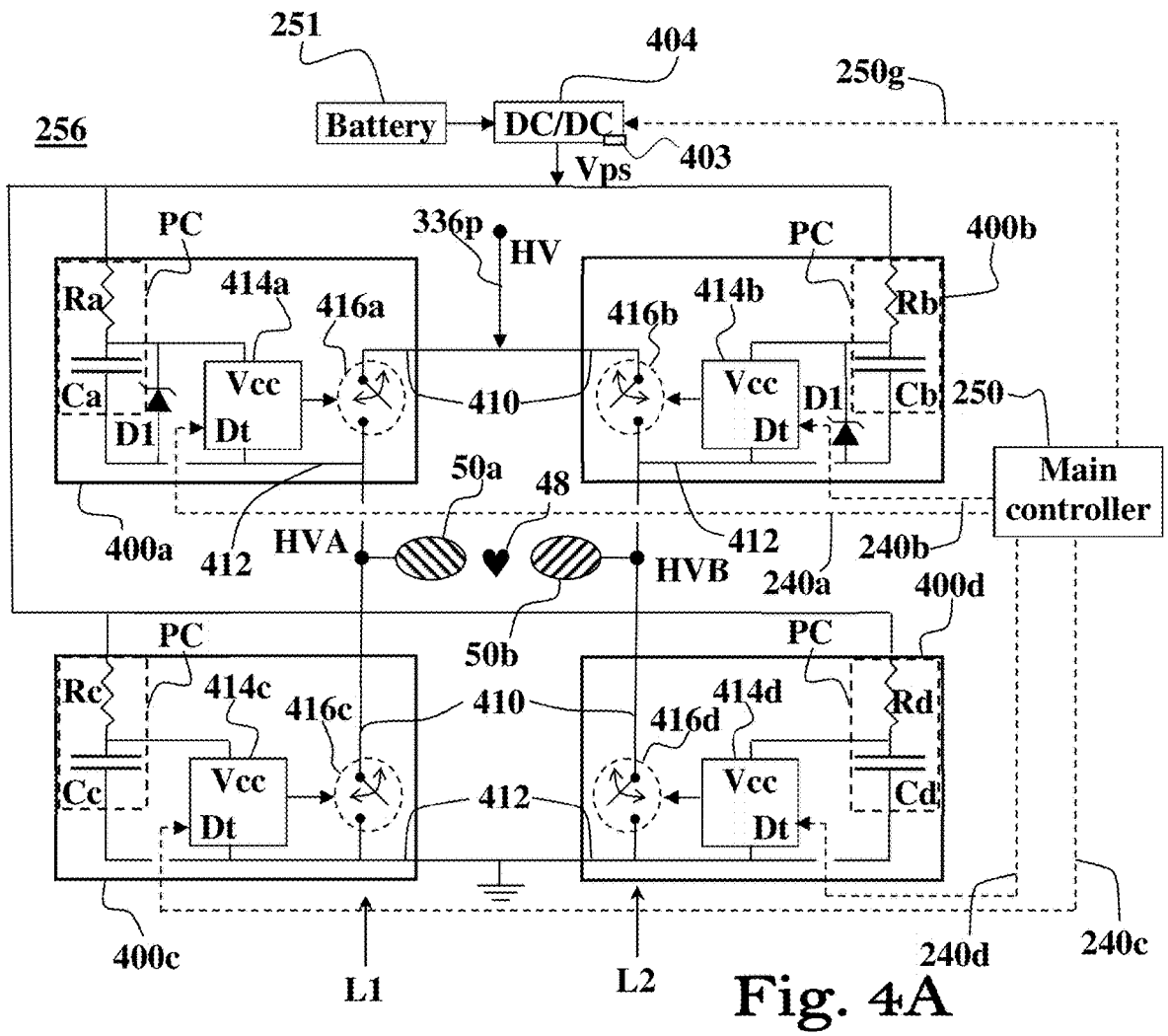
Figure 4B:
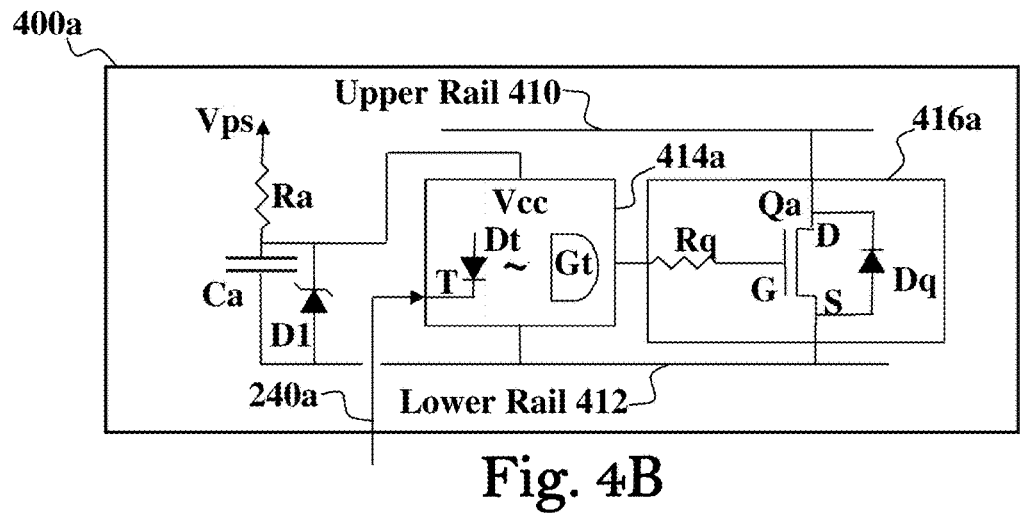
Figure 5A:
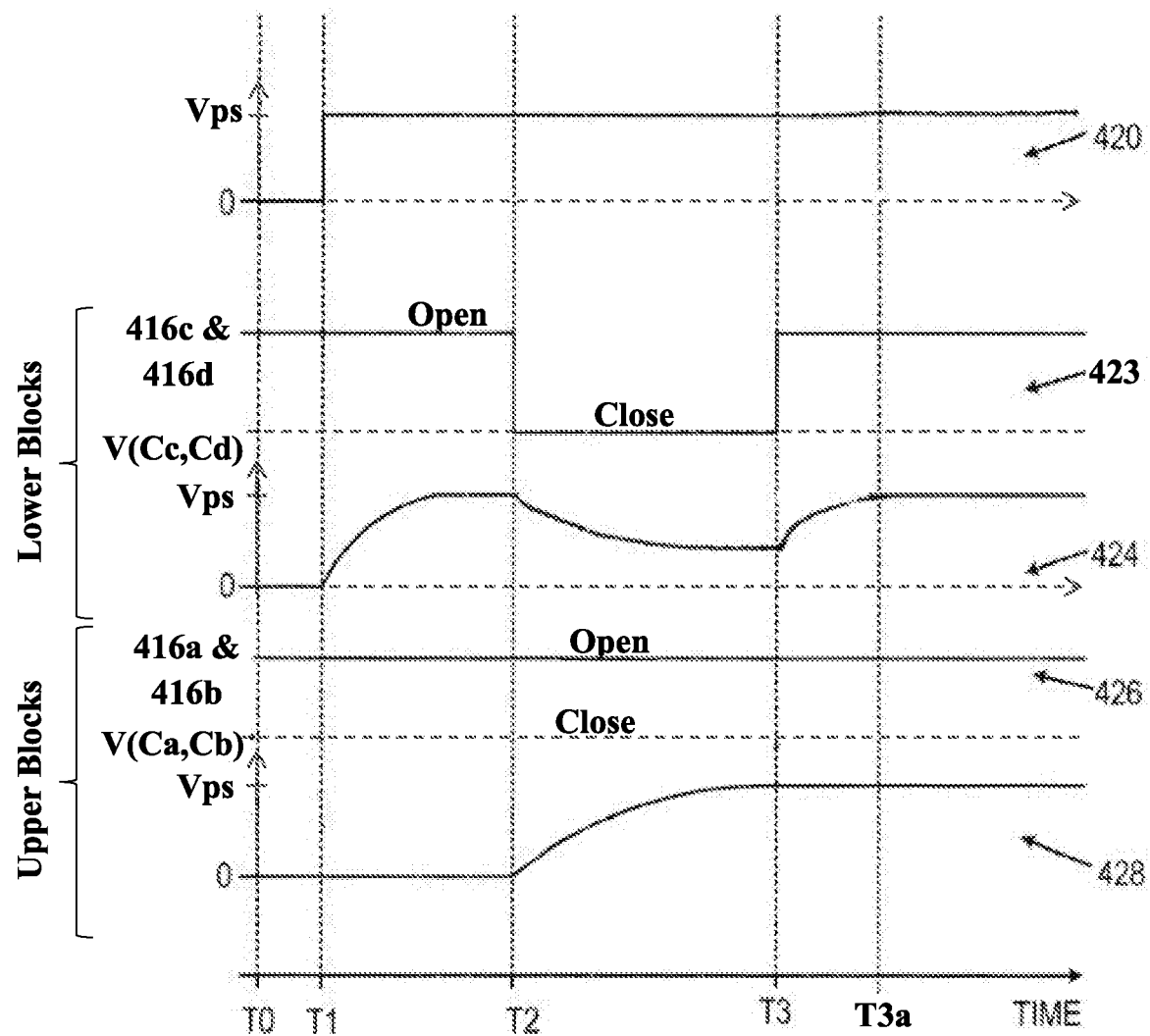
FIGS. 5A and 5B show graph plots illustrating timing logic, and the setting up and discharge of the pulse delivery unit.
Figure 5B:
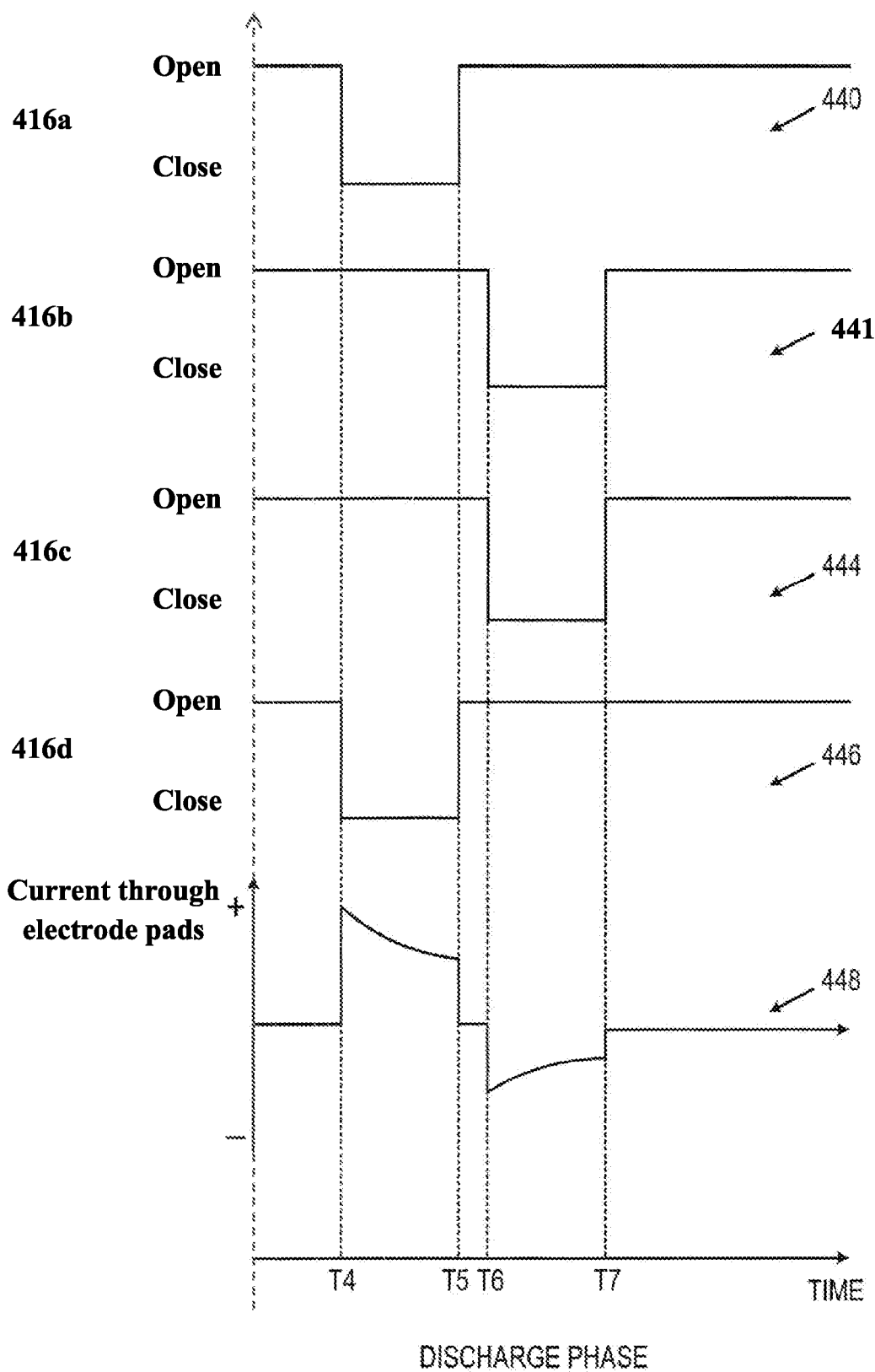

FIGS. 4A and 4B schematically illustrate the IGBT pulse delivery unit 256, according to some possible embodiments, and FIGS. 5A and 5B show graph plots illustrating possible timing logic, and the setting up and discharge of the IGBT pulse delivery unit 256, in such embodiments.

The IGBT pulse delivery unit 256 is generally used to transfer the energy stored in the capacitors bank 308 of the ESU 422 to the patient's body in a bi-phased manner, i.e., such that a portion of the stored electrical energy flows through the patient's body in one direction, and another portion of the stored energy flows through the patient's body in the opposite direction. In some possible embodiments, however, the defibrillator 44 is configured to apply the stored electrical energy to the user's body in a uni-directional manner, obviating the need for the IGBT pulse delivery unit 256, as will be apparent to those having ordinary skill in the art.

As shown in FIG. 4A, the IGBT pulse delivery unit 256 comprises four substantially similar switching/IGBT blocks 400a, 400b, 400c, and 400d (collectively referred to herein as IGBT blocks 400), constructing a H-bridge structure configured to discharge the electrical charges stored in the capacitors bank via the high voltage line 336p in a form of a bi-polar defibrillation pulse. As described in more details below, during delivery of the defibrillation pulse, the switching/IGBT blocks 400 deliver the high voltage charge stored in the capacitor bank 308 of the ESU 422 in response to respective control signals 240a, 240b, 240c and 240d (collectively referred to herein as control signals 240), received from the microcontroller 250 of the defibrillator 44. In some embodiments, activation signals 240c and 240d are applied by the microcontroller 250 prior to the application of the defibrillation pulse as part of a setup phase of the IGBT pulse delivery unit 256, as described in details hereinbelow.

The H-bridge structure of the pulse delivery unit 256 is formed by the upper IGBT blocks 400a and 400b, configured to selectively connect either electrode pad 50a or 50b, respectively, to the high voltage line 336p, via their respective switching circuitries 416a and 416b, and the lower IGBT blocks 400c and 400d, configured to selectively connect either electrode pad 50a or 50b, respectively, to the ground, via their respective switching circuitries 416c and 416d. The IGBT blocks 400 are all powered by a single power source 404 utilizing a DC-DC converter which is configured to charge, in each IGBT block 400, a powering cell PC comprising serially connected capacitive and resistive elements. The powering cell PC of each IGBT block 400 is electrically connected to a respective isolated driver 414, and configured to accumulate the electric charge for powering the isolated driver 414 which is delivering a driving current to the respective switching circuitry 416 of the IGBT block 400 for changing it into a closed (conductive) state.

The switching circuitries 416 of the IGBT blocks 400 are, typically, high voltage IGBT transistors. They form a H-bridge circuit configured to couple between the high voltage line 336p and the electrode pads 50a and 50b. The H-bridge circuit comprises a first (left) leg L1 formed by the IGBT transistors 416a and 416c serially connected to each other, and second (right) leg L2 formed by the IGBT transistors 416b and 416d serially connected to each other. As seen, at their upper sides the coupler legs L1 and L2 are electrically connected the high voltage line 336p and, at their lower sides, the coupler legs L1 and L2 are electrically connected the electrical ground. Electrode pad 50a is electrically connected to the line connecting between the IGBT transistors 416a and 416c of the first leg L1, and the electrode pad 50b is electrically connected to the line connecting between the IGBT transistors 416b and 416d of the second leg L2.

The DC/DC converter 404 of the IGBT pulse delivery unit 256 is powered by the single cell battery 251 of the defibrillator 44, and is configured to generate a voltage (Vps) of about, typically, 15 volts therefrom, for powering the IGBT drivers 414a, 414b and 414c and 414d (collectively referred to herein as isolated drivers 414) e.g., opto-electronic drivers. The powering voltage generated by the DC/DC converter 404 is sufficient for charging the driver capacitors Ca, Cb, Cc, and Cd, of the PCs, with an electric charge sufficient for driving all the respective drivers 414a, 414b, 414c and 414d, which are configured to drive their respective IGBT transistors 416a, 416b, 416c and 416d (collectively referred to herein as switching circuitries 416) e.g., utilizing solid state IGBT transistors Qa described hereinbelow with reference to FIG. 4B.

During the setup phase, the driver capacitors Ca, Cb, Cc and Cd, of the IGBT blocks 400 are charged according to a predefined charging sequence and serve as a local, limited in time length, power supply for blocks 400. After being charged in a special sequence as described herein below, driver capacitors Ca, Cb, Cc and Cd, are then used to power the drivers 414 of the IGBT blocks 400 in response to the control signals 240 from the controller 250.

It is noted that this implementation of the pulse delivery 256 unit, employing the driver capacitors Ca, Cb, Cc and Cd, to drive the derivers 414 and their respective IGBT transistors 416, requires a single DC/DC converter 404, in contrast to defibrillators of the prior art that require numerous DC/DC converters for the same task. Furthermore, as will be apparent to those having ordinary skill in the art, in this embodiment, each driver capacitor Ca, Cb, Cc and Cd, acts as a charge buffer, providing a current in the order of 100 mA for a short time duration of, typically, about 10 to 20 milliseconds, which is long enough for a biphasic defibrillation pulse. Therefore, relatively small size and capacitances capacitors Ca, Cb, Cc and Cd, can be used in the IGBT blocks 400.

The multiple DC/DC converters used in defibrillators of the prior art are typically rated at powers of the order of 15 watts each (i.e., 15 volts at 1 ampere, for driving the gate of the IGBT) or more, since they are designed to operate continuously for an indefinite period of time and not for only a few milliseconds as needed by the defibrillator. On the other hand, in the IGBT pulse delivery unit 256, the single DC/DC converter 404 is configured to provide a current in the order of 10 milliamperes at 15 Volts for a charging period of approximately 20 seconds. Consequently, the single DC/DC converter 404 (e.g., BPM15 1×1×0.4 cm DC-DC converter manufactured by muRata PS) of the IGBT pulse delivery unit 256 needs to provide only 150 milliwatts, which is two orders of magnitude smaller than the 15 watts electric power required in the defibrillators of the prior art. The reduction in the number of DC/DC converters, and the much lower power rating of the single DC/DC converter 404 of the IGBT pulse delivery unit 256, leads to significant savings in size, weight, and costs, of the IGBT pulse delivery unit 256, as compared to similar switching blocks providing bi-phased defibrillation in the defibrillators of the prior art.

FIG. 4B is a functional block diagram showing components of the IGBT block 400a. The other IGBT blocks, 400b, 400c and 400d, have substantially the same components and arrangements, and the only differences between these IGBT blocks are the connections of rails 410 and 412 of the blocks at the upper (400a and 400b) and the lower (400c and 400d) blocks, and the use of the Zenner diodes D1 for setting of the operating voltages in the upper blocks 400a and 400b. More particularly, the IGBT blocks 400a and 400b have upper rails 410 connected to the high voltage (HV) line 336p from the ESU 422, and lower rails 412 connected respectively to the defibrillation pads 50a and 50b, while the IGBT blocks 400c and 400d have the upper rails 410 connected to defibrillation pads 50a and 50b, and their lower rails 412 are connected to the ground.

The upper rails 410 of upper IGBT blocks 400a and 400b, electrically connect the high voltage terminals of their respective IGBT transistors 416a and 416b to the high voltage line 336p, and their lower rails 412 electrically connect the ground terminals of their respective IGBT transistors 416a and 416b to the ground terminals of the respective drivers (414a and 414b) and PCs of the upper IGBT blocks.

The lower rails 412 of the lower IGBT blocks 400c and 400d are electrically connected to the ground terminals of their respective IGBT transistors 416c and 416d and to the ground terminals of their respective drivers 414c and 414d, and of their respective PCs. The upper rails 410 of the lower IGBT blocks 400c and 400d are electrically connected to the high voltage terminal of their respective IGBT transistor 416 i.e., upper rail 410 of IGBT block 400c electrically connects the high voltage terminal of IGBT transistor 416c to the ground terminal of IGBT transistor 416a of IGBT block 400a, and upper rail 410 of IGBT block 400d electrically connects the high voltage terminal of IGBT transistor 416d to the ground terminal of IGBT transistor 416b of IGBT block 400b.

To operate the H bridge, driver capacitors Cc and Cd are charged directly from Vps, but, in order to charge the driver capacitors Ca and Cb, the lower rail 412 of IGBT transistors 416a and 416b must be connected to ground which is accomplished by putting IGBT transistors 416c and, respectively, 416d in a conductive state.

The PC of each of the IGBT blocks 400a, 400b, 400c and 400d, comprises a respective resistive element Ra, Rb, Rc and Rd e.g., typically, a 1 kΩ resistor, for charging the respective driver capacitor Ca, Cb, Cc and Cd e.g., typically, a 10 µF capacitor. Each driver capacitor Ca, Cb, Cc and Cd, is electrically connected between the powering (Vps) and ground terminals of a respective isolated driver 414 e.g., a 3,500 Volts isolation opto-electronic driver such as HCPL 2212 produced by Agilent Technologies of Santa Clara, Calif. With this configuration, ground terminals of the PCs of the lower IGBT blocks 400c and 400d are electrically connected to the ground via the lower rails 412 of their respective IGBT blocks 400. while the ground terminals of the PCs of the upper IGBT blocks 400a and 400b may be connected to the ground ONLY by changing the state of the switching circuitry 416 of the respective lower IGBT block 400 in the H-bridge structure i.e., the ground terminal of the PC of IGBT block 400a can be connected to the ground by closing IGBT transistors 416c of lower IGBT block 400c, and the ground terminal of the PC of IGBT block 400b can be connected to the ground by closing IGBT transistor 416d of lower IGBT block 400d.

The isolated drivers 414 receive control signals 240 from the microcontroller 250. The control signals 240 drive a light emitting diode (LED) Dt incorporated in the isolated drivers 414, which in turn triggers a gate Gt for outputting a driving current via the resistive element Rq (e.g., of about 10Ω), to the gate G of a solid state switch Qa of the IGBT transistor 416. Optionally, and in some embodiments preferably, the solid state switch Qa (typically a transistor designed for an IGBT unit) is implemented by any suitable transistor capable of withstanding the high operating voltage of approximately 2,000V, and to switch electric currents of the order of 40 Amperes for the pulse duration i.e., of about 20 milliseconds e.g., one of the 2500 Volts IGBT series produced by IXYS Corporation of Santa Clara, Calif. The drain D and the source S terminals of the solid state switch Qa are respectively connected to the upper and lower rails, 410 and 412 respectively, of the IGBT block 400.

Optionally, and in some embodiments, preferably, a protective unidirectional conducting device (diode) Dq is connected between the two rails to guarantee that electric current passes between the rails through the solid state switch Qa only from the drain D to the source S directions i.e., the protective unidirectional conducting device Dq is configured to conduct in case an electric current in the opposite direction evolves (from the lower rail 412 to upper rail 410).

FIG. 5A shows schematic timing plots of IGBT blocks 400 during the setup phase of the pulse delivery unit 256. The plot line 420 shows the voltage generated by the DC/DC converter 404, plots 423 and 426 respectively show the states (open/closed) of the lower (416c and 416d) and upper (416a and 416b) switching circuitries, plots 424 and 428 respectively show the voltages over the capacitive elements of the lower (Cc and Cd) and of the upper (Ca and Cb) IGBT blocks 400.

As seen in FIG. 4A, there is, typically, a high voltage, of about 2,000 Volts, on the upper rail 410 of the upper IGBT blocks. As described below, the setup phase of pulse delivery unit 256 is operative regardless of this high voltage. Referring back to the plots of FIG. 5A, initially, at time T0, the DC/DC converter 404 is inactive, the capacitors Ca, Cb, Cc and Cd, are not charged i.e., V(Ca, Cb, Cc and Cd)≈0 Volts, and the switching circuitries 416 are all in an open (non-conducting) state, since driving currents are not provided by the drivers 414 to the gates G of the solid state switches Qa.

At time T1 the DC/DC converter 404 receives a control signal 250g from microcontroller 250, that activates the DC/DC converter 404, which thereupon generates its output voltage Vps (plot 420) for charging the capacitive elements Cc and Cd of the PCs of the lower IGBT blocks 400c and 400d respectively which ground terminals are directly connection to the ground via their respective lower rails 412 i.e., for t>T1, V(Cc, Cd)>0 Volts. Accordingly, electric charges start to accumulate in the capacitive elements Cc and Cd of the PCs of the lower IGBT blocks 400c and 400d (plot 424), respectively, since they have a return path to the ground provided by the lower rails 412 of the IGBT blocks 400c and 400d. On the other hand, the capacitive elements Ca and Cb of the upper IGBT blocks 400*a* and 400*b*, respectively, are not charged yet since the ground terminals of their PCs have no return path to the ground via their respective lower rails 412.

At a time T2, the voltage over the capacitive elements Cc and Cd of the PCs of the lower IGBT blocks 400*c* and 400*d*, respectively, approximately reaches the voltage Vps supplied by the DC/DC converter 404, and the controller 250 generates control signals 240*c* and 240*d* to the lower isolated switches 414*c* and 414*d*, respectively, for closing the lower switching circuitries 416*c* and 416*d* (plot 423). Upon changing the states of the lower switching circuitries 416*c* and 416*d* into their closed states (i.e., electrically conducting state), a return path to the ground for the capacitive elements Cc and Cd is established, that enables them to be electrically charged, as shown in plot 428.

As seen in plot 424, driving the switching circuitries 416*c* and 416*d* by the drivers 414*c* and 414*d*, causes the capacitive elements Cc and Cd to electrically discharge until time T3, whereupon the controller 250 removes the control signals 240*c* and 240*d*, thereby removing the driving currents of the respective drivers 414*c* and 414*d* and causing the switching circuitries 416*c* and 416*d* to change back into the open state. Thereafter (t>T3), after the switching circuitries 416*c* and 416*d* are changed into the open state, the capacitive elements Cc and Cd are re-charged to reach again the voltage Vps supplied by the DC/DC converter at time T3*a*.

As plot 428 shows, at time T3 the capacitive elements Ca and Cb of the upper IGBT blocks 400*a* and 400*b*, respectively, are charged to the Vps voltage approximately, and the lower switching circuitries 416*c* and 416*d* are changed into the closed state. From time T3*a*, the capacitive elements Ca, Cb, Cc and Cd, are all fully charged to the Vps voltage, and the switching circuitries 416 are all in the open state, so that pulse delivery unit 256 is in a ready-to-discharge phase.

FIG. 5B shows timing plots illustrating switching of the pulse delivery unit 256 during the discharge phase. The plots 440, 441, 444, and 446, show the open/closed states of the switching circuitries 416 of the IGBT blocks 400. The plot 448 depicts the electric current transferred through the electrode pads (from 50*a* to 50*b*) as the pulse delivery unit 256 operates in the discharge phase to apply a defibrillation pulse to the patient's body. The discharge phase is assumed to be implemented when the capacitive elements 306 in the capacitor bank 308 of the ESU 422 (shown in FIG. 3) are fully charged e.g., to about 380 Volts.

At a time T4 the microcontroller 250, typically in response to an emergency signal received from the heart monitor 42, issues control signals 240*a* and 240*d* for the respective drivers 414*a* and 414*d* to generate driving currents for changing the upper left and the lower right switching circuitries, 416*a* and 416*d*, into the closed state, while maintaining the upper right and lower left switching circuitries, 416*b* and 416*c*, in the open state. Electric charges from the capacitor bank 308 are then discharged via the electrode pads 50*a* and 50*b* until the microcontroller 250 removes the control signals 240*a* and 240*d* at a time T5, to thereby stop the driving currents from the drivers 414*a* and 414*d*, and cause the two switching circuitries 416*a* and 416*d* to change into the open non-conductive, state.

Shortly after T5, at a time T6, the microcontroller 250 generates control signals 240*b* and 240*c* for the drivers 414*c* and 414*d* to generate driving currents to cause the upper right and the lower left switching circuitries, 416*b* and 416*c*, to change into the closed state, while maintaining the upper left and the lower right switching circuitries, 416*a* 416*d*, in the open state. In this state, electric charges are discharged from the electrode pads in the opposite direction (from 50*b* to 50*a*), until the microcontroller 250 removes the control signals 240*b* and 240*c* at a time T7, to thereby stop the driving currents generated by the drivers 414*b* and 414*c* to cause the switching circuitries 416*b* and 414*c* to change into the open state.

In some embodiments, the time intervals of each phase of the biphasic pulse generated by the pulse delivery unit 256 i.e., time intervals T4-T5, T5-T6, and T6-T7, may be preset in the defibrillator 44, according to the requirements/specifications of the user. Optionally, and in some embodiments, preferably, the time intervals T4-T5 and T6-T7 are in the range of about 5 milliseconds to 15 milliseconds, and the time interval T5-T6 is about 1 millisecond.

Figure 6A:
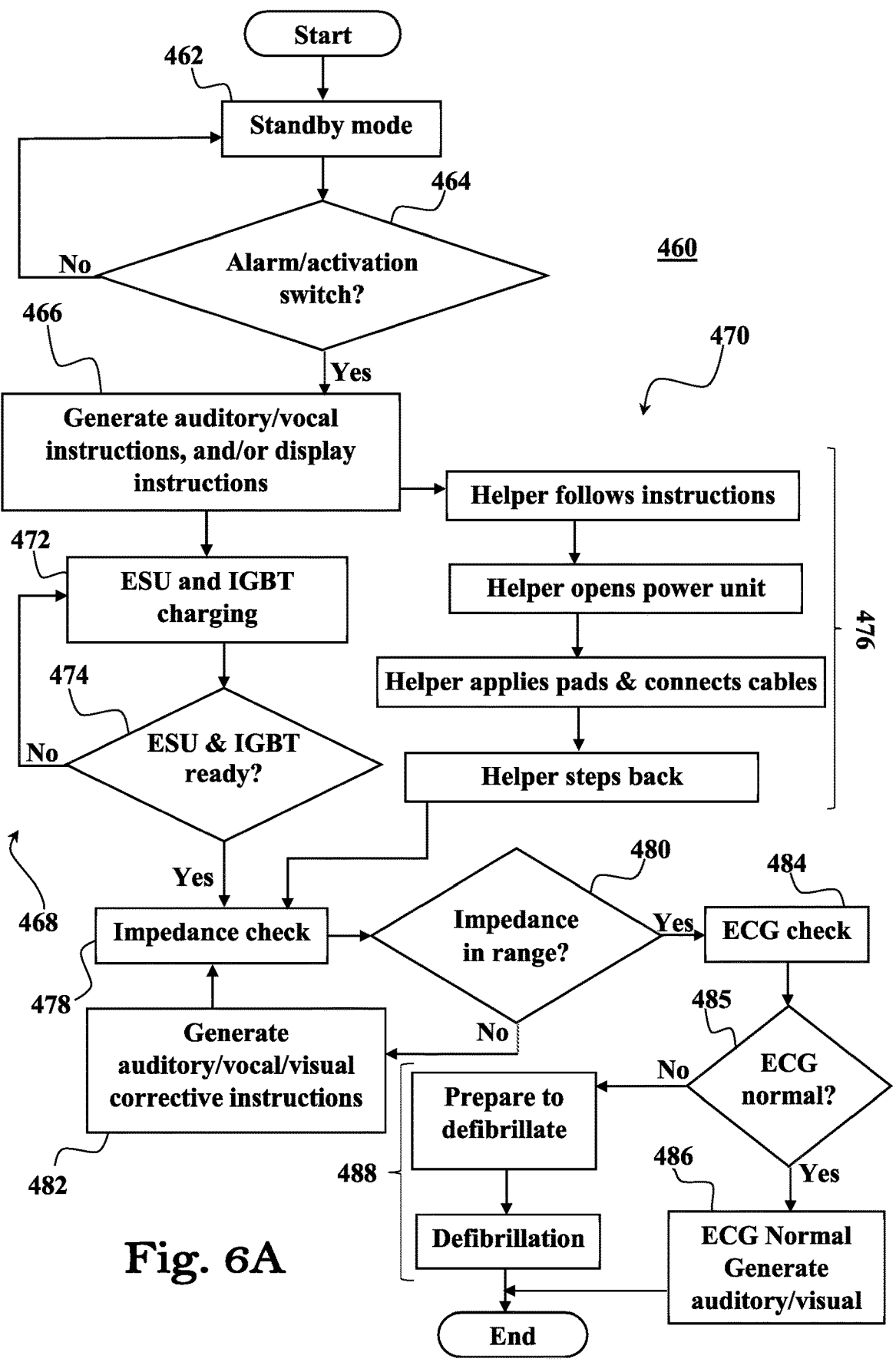

FIG. 6A is a flowchart 460 showing steps performed by defibrillator 44 during a defibrillation process according some possible embodiments, in which a helper is being available to assist the user, e.g., in case the defibrillator 44 is located adjacent to a conscious/unconscious user. The process presented in the flowchart 460 involves the heart monitor 42 e.g., utilizing an ECG harness (not shown) being worn by the user.

In an initial step 462, the defibrillator 44 is in a stand-by state, and the heart monitor 42 is operatively monitoring the state of the user. In the stand-by state, the microcontroller 250 of the defibrillator 44 is in the low power sleep mode described in details hereinabove.

In step 464, the microcontroller 250 of the defibrillator 44 checks if signals are issued by the activation switch (257) and/or if an alarm/alert signal has been received e.g., from the heart monitor 42, as described above with reference to FIG. 1C. If it is determined in step 464 that an alarm has been issued, or that activation switch 257 was activated by opening the cover 261 of the defibrillator, then, the state of the defibrillator 44 is changed into an operative emergency mode by waking up the controller 250 into a fully operational high power mode, and any other component required for the defibrillation process.

In some embodiments, step 462 is configured to operate the defibrillator 44, or the monitor 42, to wirelessly contact the smartphone of the patient/user and display on its display screen, periodically, e.g., every two weeks, a message reminding the patient/user to shave his chest for an eventual defibrillation. In other possible embodiments, the smartphone of the patient/user may call an ambulance, a landline telephone of the house of the patient/user for playing a prerecorded message indicating that the user is having "NOW! a sudden cardiac arrest and needs an immediate fibrillation.

In step 466, the defibrillator 44 displays visual instructions to the helper on the display 258 and broadcasts auditory instructions to the helper by the audio output unit 260. Optionally, and in some embodiments, preferably, the instructions are prerecorded and stored in a memory 250*m* located inside (or external to) the microcontroller 250. In some embodiments, the issued instructions are personalized, so that the helper and/or the user may be addressed and referred to by name, and the vocal instructions may use the voice of a medical professional of the user. Such personalized instructions, typically, facilitate the reactions of the helper and/or of the user in a stressful situation. Step 466 may further comprise contacting the Bluetooth module in the patient's smartphone for outputting the textual and/or auditory instructions.

After step 466, the process proceeds in two substantially simultaneous paths, 468 and 470. In path 468, in the charging step 472, the ESU 422 charges the storage capacitors 306 of the capacitor bank 308, as described hereinabove with reference to FIG. 3, and the pulse delivery unit (IGBT) 256 charges its driver capacitors, as described hereinabove with reference to FIGS. 4A and 4B. Step 474 checks if the storage capacitors of the ESU and the driver capacitors are fully charged. The time required for charging the driver capacitors is typically set to be smaller than the time required for charging the storage capacitors of the ESU to a fully charged state.

In some embodiments, step 474 is configured to ensure that the storage capacitors of the ESU are partially charged to a predefined percentage of the voltage level required for the defibrillation, described hereinabove.

In the path 470, instruction steps 476 are performed, in which the helper follows the instructions issued in step 466. Thus, in steps 476, the helper opens the cover of the defibrillator 44 to remove the defibrillation pads attached thereto. Optionally, and in some embodiments, preferably, the defibrillator starts the charging process of step 472 responsive to the opening of the cover of the defibrillator due to activation of the switch 257. In steps 476 the helper typically removes the defibrillation pads 50a and 50b from the cover 261. The helper attaches the electrode pads to the user's chest and right lateral abdomen areas, and then steps back from the user and from the electrode pads according to the provided auditory and/or visual instructions, to prevent accidental electrical discharge through the helper's body.

In step 478, the microcontroller 250 uses the impedance measurement block 262 to check that the impedance between the electrode pads 50a and 50b is within an acceptable range/preset, limits. If it is determined in step 480 that the measured body impedance is not in the acceptable range, instructions may be issued to the helper in step 482 via the display 258 and/or the audio output unit 260, to check the placement of the electrode pads and the contact quality of the electrode pads with the user's skin (when such indication is available e.g., by smart pads), and the process 460 then returns to step 478.

If it is determined in step 480 that the measured body impedance is within an acceptable range, in step 484 the microcontroller 250 checks that the ECG signals are still indicative of a fibrillation emergency situation, since, meanwhile, the ECG signals may have returned spontaneously (typically, a 5% probability) to a normal state. If it is determined in step 485 that the ECG signal 484 has returned to normal, in step 486 preset auditory and/or visual instructions are issued to the patient and/or the helper, informing them that the ECG signal is now normal. After step 486, the process 460 is ended.

If it is determined in step 485 that the measured ECG signals indicates that fibrillation is still needed, in the defibrillation step 488 the defibrillator generates control signals to the pulse delivery unit 256 to apply a defibrillation pulse to the user. The process 460 may thereafter end, or return to the initial step 462. In some embodiments, before activating the pulse delivery unit 256 in the defibrillation step 488, the storage capacitors of the ESU are charged to their full maximum voltage in order to build the voltage level required in the capacitor bank for the defibrillation.

In some embodiments, once the defibrillation pulse has been applied, the process 460 return to the capacitors charging step 472, to prepare the defibrillator to provide another defibrillation pulse to the user, if so required. Usually, up to five consecutive defibrillation pulses may be needed restore normal heart rhythm.

In some embodiments, when a heart monitor is present and is programmed to test the normality of the ECG signal, the defibrillator is configured and operable to decide about the normality of the ECG signals by comparing the ECG normality determined by the external heart monitor with a normality decision determined based on ECG signals measured by the defibrillator through the defibrillation pads. This cross-comparing process is initiated by the heart monitor and continues until successfully applying a defibrillation pulse, or until the abandonment of the process 460.

Figure 6B:
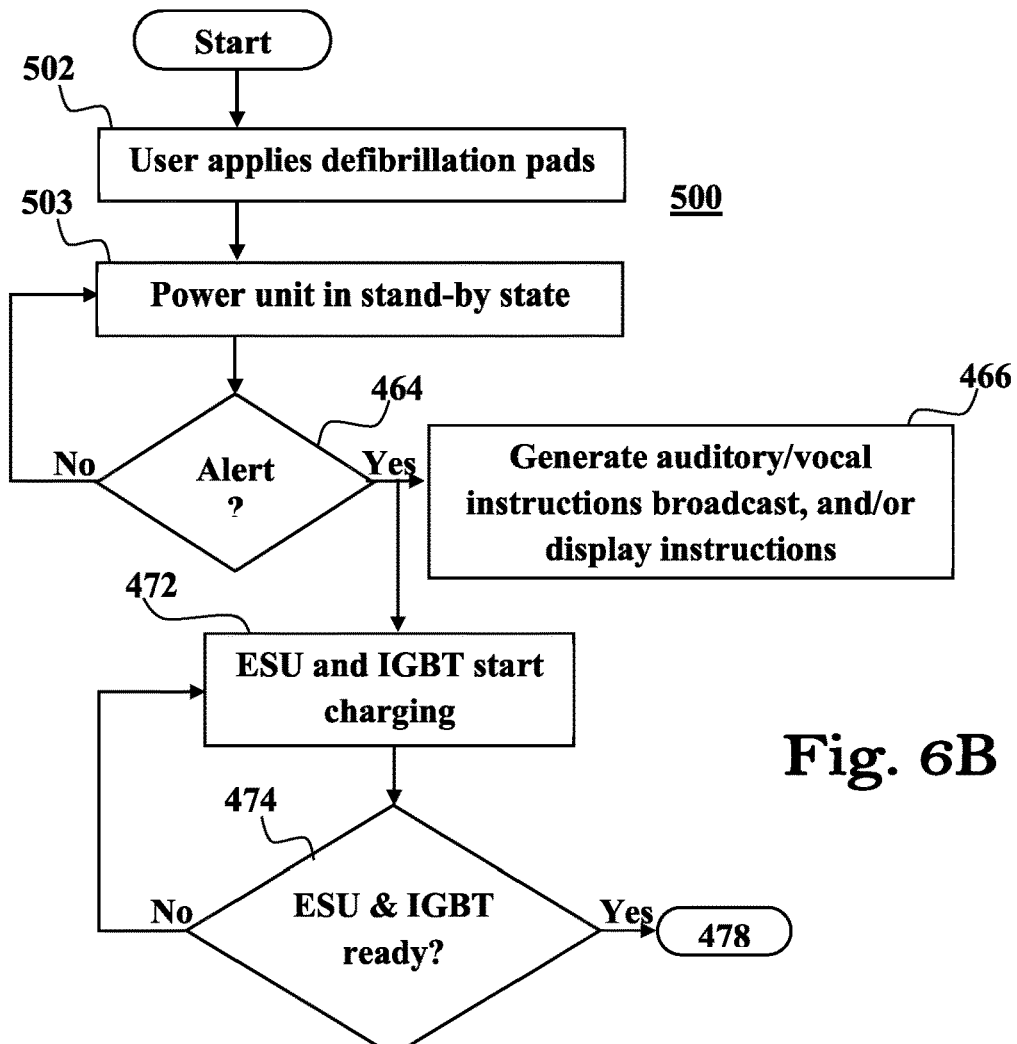

FIG. 6B shows a flowchart 500 of a process performed by defibrillator 44 when it is operated without the aid on a helper, according to some possible embodiments e.g., when the user does not have a helper available. The process 500 does not require that heart monitor 42 be operatively coupled to the body of the user.

In an initial step 502, the user attaches a secondary pair of defibrillation pads 501 to him/her-self and electrically connects the new pads 501, that are, in some embodiments, connected in parallel to the conventional pads 50a and 50b of the defibrillator 44. Typically, rather than using the conventional emergency and expensive electrode pads 50a and 50b stored in the capsule of the cover 261 of the defibrillator, in this non-limiting example the user uses a secondary pair of low cost defibrillation pads, such as regularly used in intensive care units (ICU) of hospitals. Optionally, the secondary pair of pads is substantially similar/identical to the conventional defibrillation pads 50a and 50b. It is however understood that the process 500 can be also carried out using the conventional defibrillation pads 50a and 50b.

In some embodiments, the electrical connection of the secondary pair of pads 501 to the defibrillator, electrically disconnects the conventional defibrillation pads 50a and 50b, to thereby prevent an accidental electrocution. Optionally, the electrical connection of the secondary pair of pads cause the defibrillator 44 to use the impedance measurement unit 262 to check that the impedance between the pads attached to the user's body is acceptable, and to thereby confirm that the secondary pair of pads 501 is properly situated and well applied on the user's skin. An alarms can be activated whenever the measured impedance is not within an acceptable range. Alarms may be also issued whenever determining that the inserted new pads 501 were not removed after use, which presents an electrocution hazard.

If it is determined in step 464 that an alert was issued, then in the instructions step 466 preset auditory and/or video instructions are provided to the user, generally as described hereinabove. The video instructions may refer to instructions displayed on the display unit of the defibrillator. However, in process 500 the instructions of step 466 are directed specifically to the user, since the helper is not present. Typically these instructions guide the user to lie down, and to prepare for defibrillation device. The process shown in the flowchart 500 assumes the user been previously trained how to apply the electrode pads onto his/her body by himself/herself.

The remaining steps of the process 500 are self-explanatory and substantially similar to steps referenced by the same numeral references in FIG. 6A, as described hereinabove, and will not be described herein again for the sake of brevity. However, in this non-limiting example, the instruction step 466 and the capacitors charging step 472 are conducted concurrently, as may be implemented in some possible embodiments.

Figure 6C:
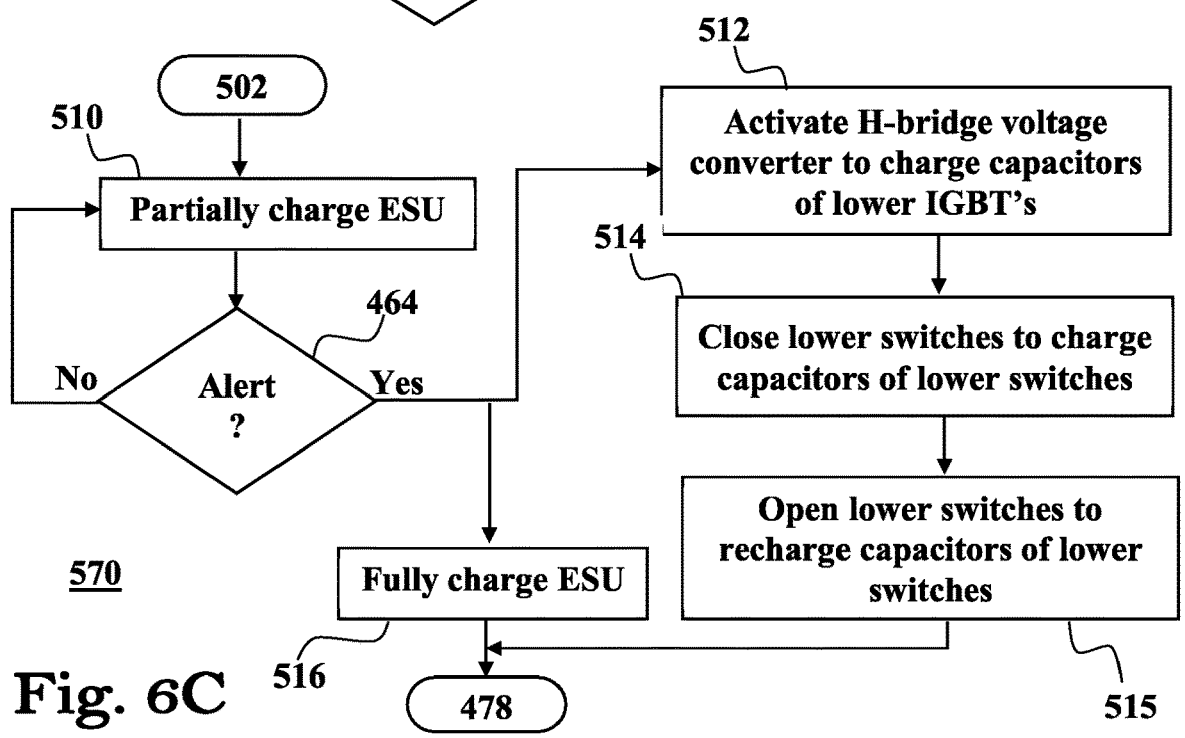

FIG. 6C is a flow chart of defibrillation process steps that may be carried out in the processes 460 and 500 described hereinabove. In this non-limiting example after, or while, the electrode pads are attached to the body of the user, in step 510 the capacitive elements of the ESU are partially charged to some predefined percentage of the voltage level required for applying defibrillation. Thereafter, whenever it is determined in step 464 that an emergency situation/alert has been issued, in step 516 the capacitive elements of the ESU are fully charged to the voltage level required for applying defibrillation, and concurrently steps 512, 514 and 515, are carried out to charge the capacitive elements of the pulse delivery unit 256.

More particularly, in step 512 the voltage converter (404) of the H-bridge coupler is activated and the capacitive elements (Cc and Cd) of the lower switching circuitries (416c and 416d) are electrically charged by the power source, as described hereinabove with reference to FIG. 4A. Thereafter, in step 514, the lower switching circuitries (416c and 416d) are changed into closed states in order to provide a path to the ground for electrically charging the driver capacitors (Ca and Cb) of the upper switching blocks 400a and 400b. After charging the driver capacitors (Ca and Cb) of the upper IGBT blocks 400a and 400b, in step 515 the states of the lower switching circuitries (416c and 416d) is changed back to the open state, and the capacitive elements (Cc and Cd) of the lower switching circuitries (416c and 416d) are recharged to restore their charged state, as described herein above with reference to FIG. 4A.

It should be understood that throughout this disclosure, where a process or method is shown or described, the steps of the method may be performed in any order or simultaneously, unless it is clear from the context that one step depends on another being performed first.

Functions of the defibrillator described hereinabove may be controlled through instructions executed by the controller 250. The controller may include, for example, one or more processors connected to a communication bus, and one or more volatile memories (e.g., random access memory—RAM) or non-volatile memories (e.g., Flash memory). A secondary memory (e.g., a hard disk drive, a removable storage drive, and/or removable memory chip such as an EPROM, PROM or Flash memory) may be used for storing data, computer programs or other instructions, to be loaded into the controller.

As described hereinabove and shown in the figured, the present invention provides a pocket size defibrillation devices and related methods/processes. While particular embodiments of the invention have been described, it will be understood, however, that the invention is not limited thereto, since modifications may be made by those skilled in the art, particularly in light of the foregoing teachings. As will be appreciated by the skilled person, the invention can be carried out in a great variety of ways, employing more than one technique from those described above, all without exceeding the scope of the claims.

The invention claimed is:

1. A handheld defibrillation device connectable to defibrillation pads and comprising:
   a small size battery cell for powering the entire defibrillator device;
   an energy storage unit comprising a plurality of serially connected capacitive elements, each of said plurality of serially connected capacitive elements configured to be electrically charged to a predefined portion of a total high voltage level needed for generating a defibrillation pulse by said handheld defibrillation device;
   a charger setup comprising a plurality of electrically isolated charging circuitries, each one of said plurality of electrically isolated charging circuitries of the charger setup being configured to independently and separately charge a respective one of said plurality of capacitive elements of the charger setup to its predefined portion of the total high voltage level for outputting by said energy storage unit said total high voltage level; and
   a pulse delivery unit configured to discharge said capacitive elements through said defibrillation pads in a desired pulse form into a body of a subject, said pulse delivery unit comprising two upper and two lower switching blocks arranged in a H-bridge structure configured to discharge electrical charges stored in the plurality of serially connected capacitive elements of the energy storage unit through the defibrillation pads in a form of a bi-polar defibrillation pulse, and wherein each switching block of the pulse delivery unit comprises a switching circuitry and a respective driver capacitive element configured to store sufficient electrical charge for generating a driving current capable of changing said switching circuitry into an electrically conducting state.

2. The device of claim 1, wherein a nominal voltage of the small size battery cell is smaller than 4 volts.

3. The device of claim 2, wherein the total high voltage level outputted by the energy storage unit is greater than 1000 volts.

4. The device of claim 1, wherein the number of serially connected capacitive elements in the energy storage unit varies according to at least one of weight and age of a subject to be defibrillated by the defibrillation device.

5. The device of claim 1, having a thickness smaller than 30 mm.

6. The device of claim 1, comprising in each of the respective plurality of electrically isolated charging circuitries of the charger setup a limiter circuitry configured to compare the voltage level over its respective capacitive element with a reference voltage and to stop the charging of said respective capacitive element whenever the voltage thereover reaches said reference voltage level.

7. The device of claim 1, wherein leakage current of each of the capacitive elements of the energy storage unit is selected to be within a 5% tolerance range, to thereby permit said energy storage unit to charge the capacitive elements without a voltage equalizing resistors ladder.

8. The device of claim 1, wherein each switching block of the pulse delivery unit comprises a controllable driver unit, and wherein the driver capacitive element of the switching block is configured to power said controllable driver unit to controllably generate the driving current for changing the state of the respective switching circuitry into the electrically conducting state.

9. The device of claim 8, comprising at least one voltage converter configured to supply electric power from the small size battery cell to each and all of the switching blocks of the pulse delivery unit for charging their driver capacitive elements.

10. The device of claim 9, wherein the at least one voltage converter comprises at least one small sized flyback converter.

11. The device of claim 1, further comprising a housing, a display unit provided in said housing, defibrillation pads and their connecting cables, and a movable cover having closed and open states, said cover being configured and arranged to accommodate said defibrillation pads and their connecting cables and to cover a portion of a display area of said display device in said closed state, to thereby provide at least part of the display visible for displaying information in said closed state.

12. The device of claim 11, wherein the cover is configured and arranged to seal the defibrillation pads and the connecting cables contained therein while in the closed state.

13. The device of claim 11, wherein the cover comprises at least one charging induction coil configured and arranged to wirelessly charge an external device adapted to couple to the defibrillation device, and support elements configured to receive and hold said external device in proximity with said charging induction coil.

14. The device of claim 1, configured to receive ECG related data from an external heart monitor configured to provide said defibrillation device said ECG related data.

15. The device of claim 1, wherein the energy storage unit is a replaceable unit configured to be replaced after either a certain amount of applied defibrillation pulses, or a certain period of time from the date of fabrication of said energy storage unit.

16. The device of claim 1, wherein the capacitive elements of the energy storage unit have a leakage current in a range of at least tens of microamperes, thereby providing a relatively short self-discharge time for preventing electrical shock hazards.

17. The device of claim 1, wherein the capacitive elements of the energy storage unit are physically attached to each other to substantially prevent replacement of a single capacitive element of the energy storage unit.

18. The device of claim 1, wherein the small size battery cell is a rechargeable battery cell, and wherein the device comprises means for wirelessly recharging said rechargeable battery cell.

19. A method of applying a defibrillation pulse via electrode pads electrically connected to the device of claim 1, the method comprising:
using the small size battery cell to separately and independently charge each of the plurality of serially connected capacitive elements of the energy storage unit by the respective plurality of electrically isolated charging units;
measuring voltage over said plurality of serially connected capacitive elements and generating measurement data indicative thereof; and
processing the measurement data and discharging electrical charges accumulated in said serially connected capacitive elements via said electrode pads after determining that the voltage over said serially connected capacitive elements reached a predetermined defibrillation voltage level.

20. The method of claim 19, further comprising:
charging the plurality of serially connected capacitive elements until a predefined standby voltage level is obtained over said serially connected capacitive elements;
receiving an indication that the defibrillation pulse is to be applied;
charging the plurality of serially connected capacitive elements until reaching said total defibrillation voltage level by said energy storage unit; and
discharging electrical charges accumulated in said serially connected capacitive elements via said electrode pads.

21. The method of claim 20, wherein the discharging of the electrical charges accumulated in the serially connected capacitive elements comprises powering the H-bridge structure by at least one voltage converter powered by the small size battery cell to form the bi-polar defibrillation pulse.

22. The method of claim 21, comprising activating the at least one voltage converter for charging the driver capacitive elements of the lower switching blocks and thereafter driving the switching circuitries of said lower switching blocks into a conductive state for charging the driver capacitive elements of the upper switching blocks.

23. The method of claim 19, comprising selecting said capacitive elements of the energy storage unit to have a leakage current within a 5% tolerance range, to thereby permit safely charging said capacitive elements without a voltage equalizing resistors ladder.

24. The method of claim 23, further comprising measuring ECG signals of the subject and applying the defibrillation pulse if the measured ECG signals are indicative of irregular heart activity.

25. The method of claim 19, wherein the charging comprises comparing the voltage over each of the serially connected capacitive elements with an allowable reference voltage, and halting operation of the respective electrically isolated charging unit used for the charging of said capacitive element whenever the voltage thereover reaches, or exceeds, said allowable reference voltage.

26. A handheld defibrillation device connectable to defibrillation pads and comprising:
a small size battery cell for supplying electrical power to all components of said handheld defibrillation device;
an energy storage unit comprising a plurality of capacitive elements;
a charger setup configured to independently and separately charge each of said plurality of capacitive elements for outputting by said energy storage unit a total high voltage level; and
a pulse delivery unit comprising:
a H-bridge structure having two upper and two lower switching blocks configured to discharge electrical charges from the plurality of capacitive elements through said defibrillation pads in a desired pulse form, each of said switching blocks comprises a switching circuitry and a respective driver capacitive element configured to store electrical charge sufficient for generating a driving electrical current capable of changing said switching circuitry into an electrically conducting state, and
at least one voltage converter configured to supply electric power from the small size battery cell to each of the switching blocks of the pulse delivery unit for charging their driver capacitive elements with electrical charge sufficient for generating a driving current for changing said switching circuitry into an electrically conducting state,
wherein ground terminals of the driver capacitive element and of the switching circuitry, of each switching block, are electrically connected to a respective rail of said switching block, a high voltage terminal of each switching circuitry of the upper switching blocks is electrically connected to the energy storage unit, a rail of each one of the upper switching blocks is electrically connected to respective one of the defibrillation pads, a high voltage terminal of the switching circuitry of each one of the lower switching blocks is electrically connected to the rail of a respective upper switching block, and the rails of the lower switching block are electrically connected to an electrical ground of the device.

27. The device of claim 26, wherein the pulse delivery unit is configured to charge the driver capacitive elements of the lower switching blocks of the H-bridge structure upon activation of the single voltage converter.

28. The device of claim 27, wherein the pulse delivery unit is configured to charge the driver capacitive elements of the upper switching blocks of the H-bridge structure after charging the driver capacitive elements of the lower switching blocks, by changing the switching circuitries of the lower switching blocks into an electrically conducting state.

29. The device of claim 28, further comprising a control unit configured and operable to activate the charging circuitries of the charger setup, to activate the voltage converter for powering the pulse delivery unit, and generate control signals for activating the lower switching blocks to charge the driver capacitive elements of the upper switching blocks after the charging of the driver capacitive elements of the lower switching blocks.

30. The device of claim 29, wherein the control unit is configured and operable to generate control signals to activate a predetermined switching sequence of the switching circuitries of the switching blocks in response to either a user input or an alarm indication received from an external device adapted to generate and communicate said alarm indication, and thereby discharge the drive capacitive elements of the energy storage unit in a form of a bi-polar defibrillation pulse.

31. The device of claim 29, wherein the control unit is configured and operable to activate the charging circuitries of the charger setup.

* * * * *